US012128079B2

(12) United States Patent
Sutton

(10) Patent No.: US 12,128,079 B2
(45) Date of Patent: *Oct. 29, 2024

(54) ENTERIC AEROBIZATION THERAPY

(71) Applicant: LPOXY THERAPEUTICS, INC., Platte City, MO (US)

(72) Inventor: Larry D. Sutton, Platte City, MO (US)

(73) Assignee: LPOXY THERAPEUTICS, INC., Platte City, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/109,718

(22) Filed: Feb. 14, 2023

(65) Prior Publication Data

US 2023/0277497 A1    Sep. 7, 2023

Related U.S. Application Data

(63) Continuation of application No. PCT/US2022/077091, filed on Sep. 27, 2022.

(Continued)

(51) Int. Cl.
*A61K 31/327* (2006.01)
*A61K 9/28* (2006.01)
(Continued)

(52) U.S. Cl.
CPC .............. *A61K 36/064* (2013.01); *A61K 9/28* (2013.01); *A61K 9/4825* (2013.01);
(Continued)

(58) Field of Classification Search
CPC ......... A61P 31/04; A61K 9/28; A61K 9/5042; A61K 9/4825; A61K 31/04; A61K 31/327;
(Continued)

(56) References Cited

U.S. PATENT DOCUMENTS 4,578,075 A    3/1986 Urquhart
4,758,075 A    7/1988 Hatano
(Continued)

FOREIGN PATENT DOCUMENTS

AU    2009299810 A1    4/2010
EP    0905086 A2    3/1999
(Continued)

OTHER PUBLICATIONS

International Search Report and Written Opinion from corresponding PCT Application No. PCT/US21/25217, 20 pages, dated Aug. 11, 2021.

(Continued)

*Primary Examiner* — Hong Yu
(74) *Attorney, Agent, or Firm* — Knobbe Martens Olson & Bear LLP

(57) ABSTRACT

Agents, kits, and methods that utilize oxygenation to prevent and/or treat intestinal inflammation and/or infections caused by anaerobic microorganisms are provided. In several embodiments, the formulations are provided as a capsule within a capsule in order to separate an oxygen prodrug from a catalyst until the formulation is at a target site within the intestine. In several embodiments, the catalyst is provided in an excess of the oxygen prodrug. In several embodiments, the prodrug is within an inner capsule or coating and a biological material comprising a catalyst (e.g., yeast, spirulina, chlorella, etc.) surrounds the encapsulated prodrug and the biological material is within a capsule or coating. The agents, kits, and methods can be utilized to prevent and/or treat anaerobic bacterial infections of the intestinal lumen by enteric aerobization therapy.

16 Claims, 16 Drawing Sheets

Related U.S. Application Data

(60) Provisional application No. 63/261,828, filed on Sep. 29, 2021.

(51) Int. Cl.
    *A61K 9/48*     (2006.01)
    *A61K 9/50*     (2006.01)
    *A61K 35/742*     (2015.01)
    *A61K 35/748*     (2015.01)
    *A61K 36/064*     (2006.01)
    *A61K 38/44*     (2006.01)
    *A61P 31/04*     (2006.01)

(52) U.S. Cl.
    CPC .......... *A61K 9/5042* (2013.01); *A61K 31/327* (2013.01); *A61K 35/742* (2013.01); *A61K 35/748* (2013.01); *A61K 38/44* (2013.01); *A61P 31/04* (2018.01)

(58) Field of Classification Search
    CPC .. A61K 35/742; A61K 35/748; A61K 36/064; A61K 38/44
    See application file for complete search history.

(56) References Cited

U.S. PATENT DOCUMENTS

| | | |
|---|---|---|
| 4,851,228 A | 7/1989 | Zentner et al. |
| 8,110,177 B2 | 2/2012 | Lin et al. |
| 10,052,288 B2 | 8/2018 | Lescure et al. |
| 10,869,834 B2 | 12/2020 | Knaus |
| 10,945,974 B2 | 3/2021 | Celiker |
| 11,179,356 B2 | 11/2021 | Celiker |
| 11,179,357 B2 | 11/2021 | Celiker |
| 11,311,573 B2 | 4/2022 | Celiker |
| 11,883,428 B2 | 1/2024 | Sutton |
| 11,944,641 B2 | 4/2024 | Sutton |
| 11,975,023 B2 | 5/2024 | Sutton |
| 2002/0001548 A1 | 1/2002 | Yoshida et al. |
| 2002/0147123 A1 | 10/2002 | Becker et al. |
| 2003/0003150 A1 | 1/2003 | Burnside et al. |
| 2003/0180360 A1 | 9/2003 | Am Ende |
| 2006/0134186 A1 | 6/2006 | Carlton et al. |
| 2007/0166373 A1 | 7/2007 | Patel |
| 2008/0159987 A1 | 7/2008 | Weinstock |
| 2011/0177138 A1 | 7/2011 | Herry et al. |
| 2011/0305738 A1 | 12/2011 | Ladizinsky |
| 2015/0017174 A1* | 1/2015 | Missbichler ..... A61K 39/39583 424/171.1 |
| 2017/0275563 A1 | 9/2017 | Federle |
| 2018/0147167 A1 | 5/2018 | Celiker |
| 2018/0221288 A1 | 8/2018 | Fukasawa et al. |
| 2019/0151238 A1* | 5/2019 | Knaus ................... A61K 9/5005 |
| 2019/0381119 A1 | 12/2019 | Ghannoum |
| 2020/0078397 A1 | 3/2020 | Celiker |
| 2020/0171123 A1 | 6/2020 | Coulter |
| 2020/0397819 A1* | 12/2020 | Ladizinsky .............. A61K 9/06 |
| 2021/0161839 A1 | 6/2021 | Celiker |
| 2021/0169829 A1 | 6/2021 | Celiker |
| 2021/0308181 A1 | 10/2021 | Sutton |
| 2022/0152097 A1 | 5/2022 | Sutton |
| 2022/0331355 A1 | 10/2022 | Celiker |
| 2023/0190794 A1 | 6/2023 | Sutton |
| 2023/0190795 A1* | 6/2023 | Sutton .................. A61K 9/4891 424/615 |
| 2023/0190840 A1* | 6/2023 | Sutton ............. C12Y 111/01006 424/93.51 |
| 2023/0270777 A1 | 8/2023 | Sutton |

FOREIGN PATENT DOCUMENTS

| | | |
|---|---|---|
| EP | 3302703 A1 | 4/2018 |
| FR | 2245668 A1 | 4/1975 |
| WO | WO2015/192136 | 12/2015 |
| WO | WO 2016/036938 | 3/2016 |
| WO | WO2016/073562 | 5/2016 |
| WO | WO 2016/196440 | 12/2016 |
| WO | WO 2017/189621 | 11/2017 |
| WO | WO2018/102469 | 6/2018 |
| WO | WO2018/132871 | 7/2018 |
| WO | WO 2019/165338 | 8/2019 |
| WO | WO 2021/202767 | 10/2021 |
| WO | 2023/007008 A1 | 2/2023 |

OTHER PUBLICATIONS

Guo, et al. "Ultrafiltration and its Applications to Sampling and Characterisation of Aquatic Colloids", Environmental Colloids and Particles: Behavior, Separation and Characterisation, 2007, in 63 pages.

Erickson, "Size and Shape of Protein Molecules at the Nanometer Level Determined by Sedimentation, Gel Filtration, and Electron Microscopy", Biological Procedures Online, vol. 11, No. 1, 2009, in 20 pages.

Malaterre, et al. "Oral osmotically driven systems: 30 years of development and clinical use" European Journal of Pharmaceutics and Biopharmaceutics, 73 (2009) 311-323.

Ashammakhi et al., "Advances in Controlled Oxygen Generating Biomaterials for Tissue Engineering and Regenerative Therapy," Biomacromolecules, 2020, vol. 21, No. 1, 56-72, Jul. 4, 2019.

Taylor et al. Hypoxia and Gastrointestinal Disease; Journal of Molecular Medicine, vol. 85, pp. 1295-1300. (Year: 2007.

Anonymous. The Free Dictionary.com; Treatment-Definition of Treatment; downloaded from: https://thefreedictionary.com/treatment on Jan. 27, 2023. (Year: 2023).

International Search Report and Written Opinion from corresponding PCT Application No. PCT/US22/077091, 18 pages, dated Nov. 10, 2022.

Felsen, "Intestinal Oxygenation in Idiopathic Ulcerative Colitis", Preliminary Report, Arch Intern Med (Chic). 1931;48(5_I):786-792.

Anonymous. An Oxygen Molecule is Smaller (Volume) Molecule Than a Nitrogen Molecule; Inertion, pp. 1-3. downloaded from: https://inertion.org/oxygen-smaller-than-nitrogen/#:-:text=Even%20though%20the%20oxygen%20molecule,N2%20is%20300%20picometers on Jul. 17, 2023. (Year: 2023).

Anonymous. The freedicionary.com; Treatment-Definition of Treatment; downloaded from https://thefreedictionary.com/treatment on Oct. 17, 2023. (Year: 2023).

Bayramoglu, G., et al., "A facile and efficient method of enzyme immobilization on silica particles via Michael acceptor film coatings: immobilized catalase in a plug flow reactor", Bioprocess and Biosystems Engineering, vol. 39, 2016, pp. 871-881.

Donell, M. The Diameter of a Water Molecule; Ozmo, pp. 1-10. downloaded from: https://www.ozmo.io/the-diameter-of-a-water-molecule/ on Jul. 17, 2023. (Year: 2023).

Enzyme Tech Information, American Laboratories, retrieved on Mar. 4, 2022, 2 pages.

Ismaiel, M. M. S., et al., "Role of pH on antioxidants production by *Spirulina (Arthrospira) platensis*", Brazilian Journal of Microbiology, vol. 47, No. 2, April-Jun. 2016, pp. 298-304.

Issa et al. Clostridium Difficile and Inflammatory Bowel Disease; Inflammatory Bowel Disease, vol. 14, pp. 1432-1442. (Year: 2008).

Ma, Y., et al., "Epsilon toxin—producing Clostridium perfringens colonize the multiple sclerosis gut microbiome overcoming CNS immune privilege", The Journal of Clinical Investigation, vol. 133, No. 9, 2023, 16 pages.

Seah, T. C. M., et al., "Purification and Properties of the Catalase of Bakers' Yeast", The Journal of Biological Chemistry, vol. 248, No. 8, Apr. 23, 1973, pp. 2889-2893.

Sun, X., et al., "Selenium Accumulation in Unicellular Green Alga Chlorella vulgaris and its Effects on Antioxidant Enzymes and Content of Photosynthetic Pigments", Plos One, vol. 9, No. 11, Nov. 6, 2014, 8 pages.

Trawczynska et al., "Biotechnology and Biotechnological Equipment," vol. 29, No. 1, 72-77 (Year: 2015).

(56) References Cited

OTHER PUBLICATIONS

Oxylife, ZerO2 Sixty, Oxygen Performance, 90 Veggie Caps (Discontinued Item), 5 pages, https://ro.iherb.com/pr/oxylife-zero2-sixty-oxygen-performance-enhancer-90-veggie-caps-discontinued-item/41426, Feb. 14, 2024.

* cited by examiner

| Study Day | Procedure |
|---|---|
| -14 | acclimation & antibiotic water |
| -13 | acclimation & antibiotic water |
| -12 | acclimation & antibiotic water |
| -11 | acclimation & antibiotic water |
| -10 | acclimation & antibiotic water |
| -9 | acclimation & antibiotic water |
| -8 | acclimation & antibiotic water |
| -7 | acclimation & antibiotic water |
| -6 | acclimation & antibiotic water |
| -5 | normal water |
| -4 | normal water |
| -3 | normal water & clindamycin |
| -2 | normal water |
| -1 | normal water |
| 0 | normal water, innoculation & begin treatment |
| 1 | treatment |
| 2 | treatment |
| 3 | treatment |
| 4 | treatment |
| 5 | observation |
| 6 | observation |
| 7 | observation |
| 8 | observation |
| 9 | observation |
| 10 | observation |
| 11 | observation |
| 12 | observation |
| 13 | observation |
| 14 | observation |

Figure 4

Clinical Observation Scale

Stools

| | |
|---|---|
| Normal | 0 |
| Slightly soft | -1 |
| soft | -2 |
| slight diarrhea | -3 |
| diarrhea | -4 | tail

| | |
|---|---|
| Normal | 0 |
| slightly wet | -1 |
| wet | -2 |

Lethargy

| | |
|---|---|
| None | 0 |
| slight lethargy | -1 |
| lethargy | -2 |

Appearance

| | |
|---|---|
| Normal | 0 |
| slight hunch | -1 |
| hunched | -2 |
| rough fur | -3 |
| slight dehydration | -4 |
| dehydration | -5 |
| dead | -6 |

Figure 6

ENTERIC AEROBIZATION THERAPY

CROSS-REFERENCE TO RELATED APPLICATIONS

This application is a continuation of International Patent Application No. PCT/US2022/077091, filed Sep. 27, 2002, which claims priority to U.S. Provisional Patent Application No. 63/261,828, filed Sep. 29, 2021, the entire contents of each of which is incorporated by reference herein.

FIELD

The present disclosure, in several embodiments, is related to aerobization therapy to prevent and/or treat anaerobic infections. Specifically, certain embodiments are related to enteric aerobization therapy to prevent and treat enteric (intestinal) anaerobic infections, although other tissue sites can also be treated.

SUMMARY

In several embodiments, formulations for prevention and/or treatment of anaerobic bacterial infection are provided. The site of action may be the intestine or other tissue. In one embodiment, the formulation comprises or consists essentially of an agent that delivers oxygen and/or acts as a source of an amount of oxygen in the patient at a target site (e.g., in the gastrointestinal tract such as the intestine), wherein the amount of oxygen is capable of creating an aerobic environment in the target site and/or converting the anaerobic enteric environment of the target site to an aerobic environment sufficient to inhibit growth, reduce toxicity, or both of the anaerobic bacterial infection. One, two or more agents may be used sequentially or simultaneously. The formulation may be adapted for oral delivery. The oral formulation, in several embodiments, is in a solid form (pills such as tablets and caplets, capsules, etc.). Pills may be round, oval, oblong, disc shaped, or other suitable shape for administration (e.g., orally). Capsules may comprise gel, solid and/or liquid components. In one embodiment, the solid formulation is particularly efficient at oxygen delivery.

In several embodiments, there is provided an oral formulation for oxygenating an intestinal region, comprising a prodrug, a plurality of yeast cells comprising catalase, a first soluble coating surrounding the prodrug and separating the prodrug from the plurality of yeast cells, a second soluble coating surrounding the plurality of yeast cells and the coated prodrug, and an insoluble, semipermeable coating having a lumen, wherein the coated plurality of yeast cells surrounding the coated prodrug reside within the lumen. In several embodiments, the prodrug comprises sodium percarbonate and/or carbamide peroxide. In several embodiments, the catalase is configured to act on the prodrug and convert it to an active agent upon contacting the prodrug. In several embodiments, the catalase controls the rate of conversion of the prodrug to oxygen. In several embodiments, the oral formulation, when orally administered to a subject, the first and second soluble coatings dissolve within an intestinal region and allow the prodrug and plurality of yeast cells to contact one another. In several embodiments, the contacting of the plurality of yeast cells and the prodrug allows the catalase from the yeast cells to convert the prodrug to oxygen, thereby oxygenating the intestinal region. In several embodiments, the oral formulation is in solid form.

In several embodiments, the prodrug is present in an amount between 100 and 2000 mg. In several embodiments, the plurality of yeast cells is provided in an amount greater than that of the prodrug, for example, between 100 and 4000 mg. In several embodiments, the oral formulation is capable of oxygenating the intestinal region after storage of the oral formulation for at least 14 days at a temperature between 15 and 30° C. In additional embodiments, the oral formulation is capable of oxygenating the intestinal region after storage of the oral formulation for at least 20, at least 25, at least 30, at least 35, or at least 40 days (or longer) at a temperature between 2° and 25° C.

In several embodiments, the plurality of yeast cells comprises one or more strains of yeast. In several embodiments, the plurality of yeast cells comprises Baker's yeast. In several embodiments, the plurality of yeast cells is from a yeast strain selected from *Saccharomyces cerevisiae, Saccharomyces exiguous, Schizosaccharomyces pombe*, and combinations thereof.

In several embodiments, there is provided an oral formulation for oxygenating an intestinal region, comprising a prodrug, a catalyst that is configured to act on the prodrug and convert it to an active agent upon contacting the prodrug, a first soluble coating surrounding the prodrug and separating the prodrug from the catalyst, a second soluble coating surrounding the catalyst and surrounding the coated prodrug and an insoluble, semipermeable coating having a lumen, wherein the coated catalyst surrounding the coated prodrug resides within the lumen. In several embodiments, the prodrug comprises sodium percarbonate. In several embodiments, the catalyst comprises catalase and the catalase controls the rate of conversion of the prodrug to oxygen. In several embodiments, the catalyst is present in an amount approximately equal to, or exceeding, an amount of the prodrug. In several embodiments, when orally administered to a subject the first and second soluble coating dissolve within an intestinal region and allow the prodrug and a catalyst to contact one another. In several embodiments, the contacting of the catalyst and the prodrug allow the catalyst to convert the prodrug to oxygen, thereby oxygenating the intestinal region. In several embodiments, the catalyst is provided by a plurality of eukaryotic, single-celled microorganisms. In several embodiments, the prodrug is present in an amount between 100 and 2000 mg and the plurality of eukaryotic, single-celled microorganisms is provided in an amount between 100 and 4000 mg. In several embodiments, the oral formulation is capable of oxygenating the intestinal region after storage of the oral formulation for at least 14 days at a temperature between 15 and 30° C.

In several embodiments, the insoluble, semipermeable coating prevents the catalase from diffusing out of the lumen and also prevents intestinal digestive enzymes from diffusing into the lumen. In several embodiments, the insoluble, semipermeable coating allows water to diffuse into or out of the lumen and allows oxygen to diffuse out of the lumen.

In several embodiments, the oral formulation, after being administered to a subject, provides 2%-5% oxygen in at least the intestinal region for 24 hours or more. In several embodiments, after being administered to a subject, the oral formulation provides 5%-10% oxygen in at least the intestinal region for 6 hours or more.

In several embodiments, the first and second soluble coatings do not substantially dissolve in stomach acid after being administered to a subject. While some dissolution may occur in some embodiments, it is not to a degree that allows for the catalase and/or yeast cells to contact and act on the prodrug. In several embodiments, the intestinal region is within a small intestine. In several embodiments, the intestinal region is with a large intestine. Other regions of the intestine are oxygenated in some embodiments.

In several embodiments, the first soluble coating comprises a gelatin capsule. In several embodiments, the second soluble coating comprises a gelatin capsule. In several embodiments, one or both of the first soluble coating and/or the second soluble coating comprises a gelatin capsule. In several embodiments, the gelatin is bovine gelatin. In several embodiments, the gelatin is porcine gelatin. In several embodiments, one or more of the first and the second soluble coating comprises a vegetable cellulose capsule. In several embodiments, the first soluble coating and/or the second soluble coating comprises an agar-agar capsule. In some such embodiments, the agar-agar is derived from seaweed. In several embodiments, the first soluble coating and/or the second soluble coating comprises an enteric coating comprising hydroxypropyl methylcellulose phthalate (HPMCP), polyvinyl acetate phthalate, diethyl phthalate, and/or cellulose acetate phthalate. In several embodiments, the prodrug is provided in tablet form.

According to several embodiments, oxygenation of the intestinal region by administration of the oral formulation prevents and/or treats an inflammatory bowel disorder (IBD). According to several embodiments, oxygenation of the intestinal region by administration of the oral formulation prevents and/or treats an intestinal anaerobic bacterial infection. In several such embodiments, the anaerobic bacteria comprise one or more of *Clostridioides difficile, Clostridium perfringens, Clostridium botulinum, Clostridium butyricum, Clostridium baratii, Vibrio cholera, Escherichia coli*, and *Salmonella enteritidis*.

In several embodiments, the oral formulation further comprises at least one excipient. In several embodiments, the at least one excipient is polyvinyl acetate and/or glyceryl behenate. In several embodiments, the oral formulation further comprises a flavorant, a sweetener, a colorant, and/or a buffer.

In several embodiments, the formulation is suitable for daily administration to a subject for at least three days.

In several embodiments, the insoluble, semipermeable coating prevents the catalase from diffusing out of the lumen, also prevents intestinal digestive enzymes from diffusing into the lumen, allows water to diffuse into or out of the lumen, and allows oxygen to diffuse out of the lumen.

Also provided for herein is an oral formulation for oxygenating an intestinal region, comprising a prodrug, comprising one or both of sodium percarbonate or carbamide peroxide, a biological material comprising catalase, a first soluble coating surrounding the prodrug and separating the prodrug from the biological material, a second soluble coating surrounding the biological material and the coated prodrug, and an insoluble, semipermeable coating having a lumen, wherein the coated biological material surrounding the coated prodrug resides within the lumen. In several embodiments, when orally administered to a subject the first and second soluble coating dissolve within an intestinal region and allow the prodrug and biological material to contact one another. In several embodiments, the contacting of the biological material and the prodrug allow the catalase from the biological material to convert the prodrug to oxygen, thereby oxygenating the intestinal region. In several embodiments, the oral formulation is in solid form.

In several embodiments, the biological material comprises a plurality of eukaryotic, single-celled microorganisms, wherein the prodrug is present in an amount between 100 and 2000 mg, wherein the plurality of eukaryotic, single-celled microorganisms is provided in an amount between 100 and 4000 mg, and wherein the oral formulation is capable of oxygenating the intestinal region after storage of the oral formulation for at least 14 days at a temperature between 15 and 30° C.

In several embodiments, the biological material comprises a plurality of cyanobacteria, wherein the prodrug is present in an amount between 100 and 2000 mg, wherein the plurality of cyanobacteria is provided in an amount between 100 and 4000 mg, and wherein the oral formulation is capable of oxygenating the intestinal region after storage of the oral formulation for at least 14 days at a temperature between 15 and 30° C. In several embodiments, the plurality of cyanobacteria are of a species selected from *Arthrospira platensis, Arthrospira fusiformis, Arthrospira* maxima, and combinations thereof.

In several embodiments, the biological material comprises fruit and/or vegetable material or a derivative thereof, wherein the prodrug is present in an amount between 100 and 2000 mg, wherein the fruit or vegetable material or derivative thereof is provided in an amount between 100 and 4000 mg, and wherein the oral formulation is capable of oxygenating the intestinal region after storage of the oral formulation for at least 14 days at a temperature between 15 and 30° C. In several embodiments, the biological material comprises vegetable material or a derivative thereof and is from a cruciferous vegetable. In several embodiments, the biological material comprises vegetable material or a derivative thereof and is from alfalfa, Brussel sprouts, young sprouts of dark green plants, leeks, onions, broccoli, parsnips, zucchini, spinach, kale, radishes, carrots, red peppers, turnips, cucumbers, celery, avocado, potato, and/or red cabbage. In several embodiments, the biological material comprises fruit material or a derivative thereof and is from kiwi, peaches, cherries, apricots, bananas, watermelon, pineapple, apples and/or grapes.

Also provided herein is an oral formulation, comprising an insoluble, semipermeable external coating having a lumen, a prodrug comprising sodium percarbonate or carbamide peroxide positioned within the lumen, a first soluble coating surrounding the prodrug, a catalyst comprising catalase positioned within the lumen and surrounding the prodrug coated with the first soluble coating, a second soluble coating surrounding the catalyst, wherein, when orally administered to a subject, water from intestinal fluid diffuses through the insoluble, semipermeable external coating and dissolves the first and second soluble coatings, thereby allowing the catalyst to contact the prodrug and act on the prodrug to produce oxygen, thereby oxygenating the intestinal region.

In several embodiments, the insoluble, semipermeable coating prevents the catalase from diffusing out of the lumen, also prevents intestinal digestive enzymes from diffusing into the lumen, allows water to diffuse into or out of the lumen, and allows oxygen to diffuse out of the lumen. In several embodiments, the first soluble coating and/or the second soluble coating comprises a gelatin capsule. In several embodiments, the prodrug is in tablet form and coated with a gelatin coating, and wherein the second soluble coating comprises a gelatin capsule. In several embodiments, the prodrug comprises sodium percarbonate and is present in an amount between 100 and 2000 mg, wherein the catalyst is provided by a plurality of yeast cells, and wherein the plurality of yeast cells are present in an amount equal to, or in excess of, the sodium percarbonate.

Also provided for herein is a method of oxygenating a region of an intestine for prevention and/or treatment of an inflammatory bowel disorder (IBD) comprising administering at least one dose of an oral formulation provided for herein.

Also provided for herein is a method of oxygenating a region of an intestine for prevention and/or treatment of an intestinal anaerobic bacterial infection comprising administering at least one dose of an oral formulation provided for herein.

Also provided for herein is a use of an oral formulation disclosed herein for the treatment of an inflammatory bowel disorder (IBD) or an intestinal anaerobic bacterial infection.

Also provided for herein is a use of an oral formulation disclosed herein in the manufacture of a medicament for the treatment of an inflammatory bowel disorder (IBD) or an intestinal anaerobic bacterial infection.

In several embodiments, there is provided a method of oxygenating a region of an intestine, comprising orally administering to a subject an oral formulation, the oral formulation comprising an insoluble, semipermeable external coating having a lumen, a prodrug comprising sodium percarbonate or carbamide peroxide positioned within the lumen, a first soluble coating surrounding the prodrug, a catalyst comprising catalase positioned within the lumen and surrounding the prodrug coated with the first soluble coating, and a second soluble coating surrounding the catalyst.

In several embodiments, when orally administered to a subject, water from intestinal fluid diffuses through the insoluble, semipermeable external coating and dissolves the first and second soluble coatings, thereby allowing the catalyst to contact the prodrug and act on the prodrug to produce oxygen, resulting in oxygenation of the intestinal region. In several embodiments, at least one additional oral administration of the oral formulation is performed.

In several embodiments, the catalase is provided by a biological material.

In several embodiments, the biological material comprises a plurality of eukaryotic, single-celled microorganisms. In several embodiments, the plurality of eukaryotic, single-celled microorganisms comprises a plurality of yeast cells from one or more strains of yeast. In several embodiments, the plurality of yeast cells comprises Baker's yeast. In several embodiments, the plurality of yeast cells are from a yeast strain selected from *Saccharomyces cerevisiae, Saccharomyces exiguous, Schizosaccharomyces pombe*, and combinations thereof.

In several embodiments, the biological material comprises a plurality of cyanobacteria, wherein the plurality of cyanobacteria are of a species selected from *Arthrospira platensis, Arthrospira fusiformis, Arthrospira* maxima, and combinations thereof.

In several embodiments, the biological material comprises fruit and/or vegetable material or a derivative thereof. In several embodiments, the biological material comprises vegetable material or a derivative thereof and is from a cruciferous vegetable, wherein the biological material comprises vegetable material or a derivative thereof and is from alfalfa, Brussel sprouts, young sprouts of dark green plants, leeks, onions, broccoli, parsnips, zucchini, spinach, kale, radishes, carrots, red peppers, turnips, cucumbers, celery, avocado, potato, and/or red cabbage, and/or wherein the biological material comprises fruit material or a derivative thereof and is from kiwi, peaches, cherries, apricots, bananas, watermelon, pineapple, apples and/or grapes.

In several embodiments, the prodrug is present in an amount between 100 and 2000 mg, wherein the oral formulation is capable of oxygenating the intestinal region after storage of the oral formulation for at least 14 days at a temperature between 15 and 30° C.

In several embodiments, the catalase, the biological material, the plurality of yeast cells, the plurality of cyanobacteria, and/or the fruit and/or vegetable material or a derivative thereof is provided in an amount between 100 and 4000 mg.

In several embodiments, wherein the oral formulation is capable of oxygenating the intestinal region after storage of the oral formulation for at least 20 days at a temperature between 2° and 25° C.

In several embodiments, when administered to a subject, the formulation provides 2%-5% oxygen in at least the intestinal region for 24 hours or more. In several embodiments, when administered to a subject, the formulation provides 5%-10% oxygen in at least the intestinal region for 6 hours or more.

In several embodiments, the intestinal region is within a small intestine or a large intestine of the subject.

In several embodiments, the first soluble coating and/or the second soluble coating comprises a gelatin capsule, wherein the gelatin is optionally bovine or porcine gelatin. In several embodiments, one or more of the first and the second soluble coating comprises a vegetable cellulose capsule, or wherein the first soluble coating and/or the second soluble coating comprises an agar-agar capsule, wherein the agar-agar is derived from seaweed. In several embodiments, the first soluble coating and/or the second soluble coating comprises an enteric coating comprising hydroxypropyl methylcellulose phthalate (HPMCP), polyvinyl acetate phthalate, diethyl phthalate, and/or cellulose acetate phthalate.

In several embodiments, of the methods, oxygenation of the intestinal region by administration of the oral formulation prevents and/or treats an inflammatory bowel disorder (IBD). In several embodiments, oxygenation of the intestinal region by administration of the oral formulation prevents and/or treats an intestinal anaerobic bacterial infection.

In several embodiments, the insoluble, semipermeable coating prevents the catalase from diffusing out of the lumen, also prevents intestinal digestive enzymes from diffusing into the lumen, allows water to diffuse into or out of the lumen, and allows oxygen to diffuse out of the lumen. In several embodiments, the insoluble, semipermeable coating is substantially the only portion of the oral formulation passed by the subject in a bowel movement subsequent to administration of the oral formulation.

In several embodiments, the oral formulations provided for herein do not require refrigeration or freezing to remain stable prior to administration.

In additional embodiments, an agent, such as the active pharmaceutical ingredient (API), may comprise or consist essentially of oxygen carrier molecules and/or oxygen containing mixtures. The oxygen carrier molecules and/or oxygen containing mixtures include, for example, oxygen binding biomolecule, oxygen cocktail, microemulsions of oxygen gas bubbles, microemulsions of oxygen gas foams, or perfluorocarbons (e.g., oxygen perfluorocarbon solutions). The agent may comprise or consist essentially of oxygen prodrugs or oxygen generating compounds. The oxygen prodrug or oxygen generating agent includes, for example, an oxygen generating metal-peroxide salt, a hydrogen peroxide complex (including for example, a hydrogen peroxide adduct or a peroxide-containing organic molecule).

The formulations described herein, in several embodiments, provide an oxygen concentration and/or an amount of oxygen of at least (i) 2-5% oxygen (gas phase) for 24 hours or more or (ii) 5-10% oxygen (gas phase) for 6 hours or more. In one embodiment, oxygen is increased by at least 20% at the target site for 1-24 hours, or more. The formulations may be used prophylactically by administration daily or several times per week. Conditions such as IBD may be significantly improved by the formulations described herein by treating (or preventing) the anaerobic microbial growth that exacerbates IBD symptoms.

In several embodiments, a catalyst is also provided. In several embodiments, a formulation is provided in which the catalyst is encapsulated or otherwise contained within means for controlling or regulating diffusion. The API may also be encapsulated or otherwise contained within means for controlling or regulating diffusion. Such means include, for example, a material or layers of material, such as a membrane, coating or other material. In one embodiment, the material is permeable to water, but impermeable to one or more solutes. For example, the material may be permeable to water, but impermeable to solutes with molecular weights >250, 500, 1000, 1500 or higher Daltons. In one embodiment, either the catalyst (such as catalase) or the API is encapsulated or coated. In another embodiment, both are encapsulated or coated (e.g., individually). For example, in several embodiments, the catalyst and/or the API is individually coated or encapsulated in granular or powder form. As an example, granules of the catalyst and/or API are contained within a capsule or other enclosure, wherein each of the granules is coated (such as with one, two or more of an enteric coating, an osmotic coating, and a barrier coating). Two or more layers of the same coating may also be used. In some embodiments, each granule is individually coated, and then the coated granules are contained within a capsule or other form. In other embodiments, each granule is individually coated and no capsule or other enclosure is provided. In one embodiment, group of granules are coated (e.g., 2-20 granules) and then optionally placed in a capsule or some other form.

In one embodiment, the means for controlling or regulating diffusion (such as the material described herein) (i) permits the diffusion of water, electrolyte, certain solutes and/or oxygen across the material, (ii) prevents all, substantially all or a majority of catalase (or other agent) from diffusing out of the material and (iii) prevents all, substantially all or a majority of digestive enzymes from diffusing into the material. In some embodiments, the agent comprises or consists essentially of oxygen carrier molecules and/or oxygen containing mixtures. In one embodiment, such catalyst (such as catalase) or other agent (such as the API) is formulated within a dialysis or osmotic membrane coated capsule or tablet. In one embodiment, the pore size of the membrane is of sufficient size to allow small molecules like water, electrolyte, certain solutes and oxygen to diffuse across the membrane, but small enough to prevent catalase from diffusing out of the capsule or tablet while also preventing digestive enzymes from diffusing into the capsule or tablet. In one embodiment, the pore size ranges from 1 nanometer to 100 micrometers (e.g., 10-250 nanometers, 100-500 nanometers, 500-1000 nanometers, 1-100 micrometers, and overlapping ranges therein) or 1 kiloDalton to 100 kiloDaltons (e.g., 1-10 kD, 10-50 kD, 50-100 kD, and overlapping ranges therein). Less than about 1000 Daltons is used in one embodiment (e.g., 10-100 Daltons, 100-500 Daltons, 250-750 Dalton, 500-1000 Daltons, and overlapping ranges therein). Layers of coating, membrane or other material may be used wherein, for example, the functional pore size is smaller than the actual pore size due to the layering. In some embodiments, the material comprises polymers (e.g., cellulose compounds).

In several embodiments, a formulation for prevention, treatment, or both of at least one infection (e.g., intestinal anaerobic bacterial infection) is provided, comprising at least one agent that delivers oxygen and/or acts as a source of an amount of oxygen at the target site (e.g., gastrointestinal tract such as in the intestine) when administered to a subject, wherein the amount of oxygen is capable of creating an aerobic environment in the target site and/or converting the anaerobic enteric environment of the target site to an aerobic environment sufficient to inhibit growth, reduce toxicity, or both of the anaerobic bacterial infection. The agent may comprise or consist essentially of oxygen carrier molecules and/or oxygen containing mixtures. Oxygen carrier molecules and/or oxygen containing mixtures may comprise or consist essentially of an oxygen binding biomolecule, oxygen cocktail, microemulsions of oxygen gas bubbles, microemulsions of oxygen gas foams, or oxygen perfluorocarbon solutions. The oxygen binding biomolecule may comprise or consist essentially of one, two or all of leghemoglobin, hemoglobin and/or myoglobin. In some embodiments, the formulation additionally comprises one or more additional components that enhance localization, increase stability and/or reduce degradation of the agents described herein. The formulation may be designated as GRAS.

In several embodiments, the agent comprises or consists essentially of oxygen prodrugs or oxygen generating compound, or both. The oxygen prodrug or oxygen generating agent may comprise or consist essentially of an oxygen generating metal-peroxide salt or a hydrogen peroxide complex. The oxygen generating metal-peroxide salt or a hydrogen peroxide complex may comprise or consist essentially of carbamide peroxide, calcium peroxide, calcium hydroxide, magnesium peroxide, sodium percarbonate, or an endoperoxide, or combinations thereof.

In several embodiments, the formulation comprises or consists essentially of a catalyst to control the rate of conversion of an API (such as a peroxide containing prodrug) to oxygen. The catalyst may comprise or consist essentially of iodide, catalase, manganese dioxide, iron (III), silver, or dichromate, or combinations thereof. The optional catalyst may be administered in the same formulation as the API, or separately. In several embodiments, the formulation comprises an API at about 100 to 3000 mg per dose (e.g., 100 to 500 mg, 250 to 2000 mg, 500 to 1000 mg, 500 to 1500 mg, 750 to 1000 mg, 800 to 1200 mg, 1000 to 2000 mg, and overlapping ranges therein) with an optional catalyst at about 5 to 1000 Baker units (e.g., 5 to 25 Baker units, 10 to 100 Baker units, 10 to 150 Baker units, 25 to 50 Baker units, 50 to 150 Baker units, 150 to 300 Baker units, 300 to 500 Baker units, 250 to 750 Baker units, 500 to 1000 Baker units, and overlapping ranges therein). The formulation may be provided once daily, 2-6 times daily or as needed. In one embodiment, the API comprises at least one of sodium percarbonate and carbamide peroxide and the catalyst comprises catalase. The ratio of the API to the catalyst (e.g., by weight) is about 1:1, 1:2, 1:3, 1:4, 4:1, 3:1, or 2:1 in some embodiments. In one embodiment, the API:catalyst ratio is 5:1 to 30:1 (e.g., May 10, 2015/20/25/30:1). The formulation may also comprise inactive ingredients such as one or more of the following: acacia gum, rice flour, cellulose, stearates (e.g., magnesium stearate), gelatin, carbonates (e.g., calcium carbonate) and other various binders, excipients, stabilizers, and pH balancers. The formulation may be provided as pills such as tablets and caplets, capsules, etc. and the like. The percentage of inactive ingredients in a dose (such as an oral dose, by weight) is about 25-75%. Oral formulations or supplements may be divided into smaller sized pills (and the like) for swallowability (e.g., a dose or serving size may be 2, 3 or more smaller pills such as tablets and caplets, capsules, etc., which may be partially or wholly in solid form. The formulation, in some embodiments, is in a solid form for oral delivery such as tablets, caplets, capsules, etc., which may be coated or uncoated. Alternatively, gel and liquid oral formulations may be used. Administration via non-oral routes is also provided in some embodiments.

Also provided herein are kits for the prevention, treatment or both of at least one anaerobic infection (e.g., of the intestine or other region), wherein the kit comprises a formulation described herein and instructions for use.

A method of prevention, treatment, or both of at least one infection of a target site (e.g., an anaerobic infection of the gastrointestinal tract such as the intestine) is provided in several embodiments. In one embodiment, the method comprises or consists essentially of administering (e.g., orally) a therapeutically effective amount of a formulation described herein to a subject (e.g., patient) in need thereof, delivering an amount of oxygen in the intestine (or other site in the body), wherein said amount of oxygen is provided in an amount that is sufficient to (i) create an aerobic environment in the target site and/or (ii) convert the anaerobic enteric environment of the target site to an aerobic environment capable of inhibiting growth, reducing toxicity, or both of the anaerobic bacterial infection. The method administration may be provided for hours, days, weeks, months or longer. The subject may be instructed to orally ingest the formulation 1-6 times per day for at least 3, 7, 10 or 14 days. The subject may be instructed to orally ingest the formulation 1-3 times per day for several weeks, months or longer as a prophylactic. Solid formulations for oral delivery, such as pills and capsules, are provided in several embodiments.

The anaerobic infection of the intestine (or other site in the body) may be caused by a *Clostridioides difficile* infection and/or a foodborne infection. The foodborne infection may be caused by a bacterium selected from the group consisting of one or more of *Clostridium perfringens*, botulism caused by *Clostridium botulinum, Clostridium butyricum*, and *Clostridium baratii*, cholera caused by *Vibrio cholera*, diarrheagenic *Escherichia coli* infection, and *Salmonella enteritidis*.

In several embodiments, there is provided an oral granular formulation for treating an intestinal anaerobic bacterial infection, comprising a plurality of granules or particles comprising an agent and a catalyst, wherein the agent is configured to produce oxygen upon being acted on by the catalyst and wherein the catalyst controls the rate of conversion of the agent to oxygen, a first coating on an exterior of each granule, wherein the first coating is resistant to degradation in low pH environments; a second coating between the first coating and the catalyst, and wherein the second coating allows for water to contact and activate the catalyst upon at least partial degradation of the first coating.

In several embodiments, when orally administered to a subject, the agent provides said oxygen to an intestine of the subject to create an aerobic environment in the intestine sufficient to inhibit growth of a population of anaerobic bacteria that caused an anaerobic bacterial infection in the intestine.

In several embodiments, the granules or particles are optionally contained in a capsule.

In several embodiments, the agent comprises sodium percarbonate or carbamide peroxide, or a combination thereof. In several embodiments, the catalyst comprises catalase.

In several embodiments, further comprising a third coating, wherein the third coating is a barrier between the agent and the catalyst. In several embodiments, the first coating is resistant to degradation in the stomach of a subject, thereby allowing the granules to be delivered to the intestine without being substantially inactivated by gastric acid. In several embodiments, the granules or particles further comprise one or more binding agents, one or more dispersants, one or more glidant and/or plasticizer. In several embodiments, the oral formulations do not comprise a tannin or tannin-like component.

In several embodiments, there is provided a coated oral formulation in solid form for treating an intestinal anaerobic bacterial infection, comprising an agent and a catalyst, wherein the agent comprises sodium percarbonate or carbamide peroxide, wherein the catalyst comprises catalase, wherein the catalase controls the rate of conversion of the agent to oxygen, wherein when orally administered to a subject, the agent provides said oxygen to an intestine of the subject to create an aerobic environment in the intestine sufficient to inhibit growth of a population of anaerobic bacteria that caused an anaerobic bacterial infection in the intestine, and wherein the agent is provided as individually coated granules or groups of granules and wherein the granules are optionally provided in a capsule.

In several embodiments, the population of anaerobic bacteria comprises *Clostridioides difficile*.

In several embodiments, when administered to a subject, the agent provides 2-5% oxygen in at least a portion of the intestine for 24 hours or more. In several embodiments, the agent provides 5-10% oxygen in at least a portion of the intestine for 6 hours or more.

In several embodiments, the catalase is contained within a material, wherein the material prevents at least a majority of the catalase from diffusing out of the material, and wherein the material prevents at least one intestinal digestive enzyme from diffusing into the material. In several embodiments, the catalase is encapsulated in a porous membrane that controls diffusion of the catalase across said membrane.

In several embodiments, the agent is provided in a range of 250 to 2000 mg. In several embodiments, the catalase is provided in a range of 10 to 150 Baker units.

Several embodiments, provide for an oral formulation in solid form for treating an intestinal anaerobic bacterial infection, comprising an agent and a catalyst, wherein the catalyst controls the rate of conversion of the agent to oxygen, wherein, when orally administered to a subject, the agent provides said oxygen to an intestine of the subject to create an aerobic environment in the intestine sufficient to inhibit growth of a population of anaerobic bacteria that are capable of causing an anaerobic bacterial infection in the intestine, and wherein the population of anaerobic bacteria comprises *Clostridioides difficile*; and wherein the oral formulation is in a solid form.

In several embodiments, the agent comprises sodium percarbonate. In several embodiments, the agent comprises carbamide peroxide. In several embodiments, the catalyst comprises catalase. In several embodiments, the catalyst is encapsulated in a membrane that controls diffusion of the catalyst across said membrane.

Also provided for herein is an oral formulation in solid form for treating an intestinal anaerobic bacterial infection, comprising at least one agent that delivers oxygen or acts as a source of oxygen in an intestine when administered to a subject, wherein said at least one agent is in a solid form, wherein the oxygen is capable of creating an aerobic environment in the intestine sufficient to treat the anaerobic bacterial infection by reducing a population of anaerobic bacteria. In several embodiments, the oral formulation further comprises a catalyst that controls the rate of conversion of the agent to oxygen. In several embodiments, the catalyst is coated by a material that prevents at least a majority of the catalyst from diffusing out of the material, and wherein the material prevents at least one digestive enzyme located in the intestine from diffusing into the material. In several embodiments, the delivered oxygen increases the oxygen level in the intestine by at least 20% for 1-24 hours.

In several embodiments, the agent comprises sodium percarbonate. In several embodiments, the agent comprises carbamide peroxide. In several embodiments, the agent is provided in a range of 250 to 2000 mg.

In several embodiments, an oral granular formulation for treating an intestinal anaerobic bacterial infection, comprising a plurality of granules or particles comprising an agent and a catalyst, wherein the agent comprises sodium percarbonate or carbamide peroxide, wherein the catalyst comprises catalase, and wherein the catalase controls the rate of conversion of the agent to oxygen; a first coating on an exterior of each granule, wherein the first coating is resistant to degradation in low pH environments; a second coating between the first coating and the catalyst, wherein the second coating allows for water to contact and activate the catalyst upon at least partial degradation of the first coating; wherein when orally administered to a subject, the agent provides said oxygen to an intestine of the subject to create an aerobic environment in the intestine sufficient to inhibit growth of a population of anaerobic bacteria that caused an anaerobic bacterial infection in the intestine, and wherein the granules or particles are optionally contained in a capsule.

In several embodiments, the oral formulation further comprises a third coating, wherein the third coating is a barrier between the agent and the catalyst. In several embodiments, the first coating is resistant to degradation in the stomach of a subject, thereby allowing the granules to be delivered to the intestine without being substantially inactivated by gastric acid. In several embodiments, the oral formulation further comprises one or more binding agents, one or more dispersants, one or more glidant and/or plasticizer. In several embodiments, the formulation does not comprise a tannin or tannin-like component. In several embodiments, the formulations, kits and methods described herein may be used for the treatment of Inflammatory Bowel Disease (IBD) and/or prophylaxis against exacerbation of IBD.

BRIEF DESCRIPTION OF THE DRAWINGS

FIG. 4 depicts one non-limiting embodiment of a study design of a mouse model of *Clostridioides difficile* infection.

FIG. 6. depicts one non-limiting embodiment of a clinical observation scale.

DETAILED DESCRIPTION

Figure 1A:
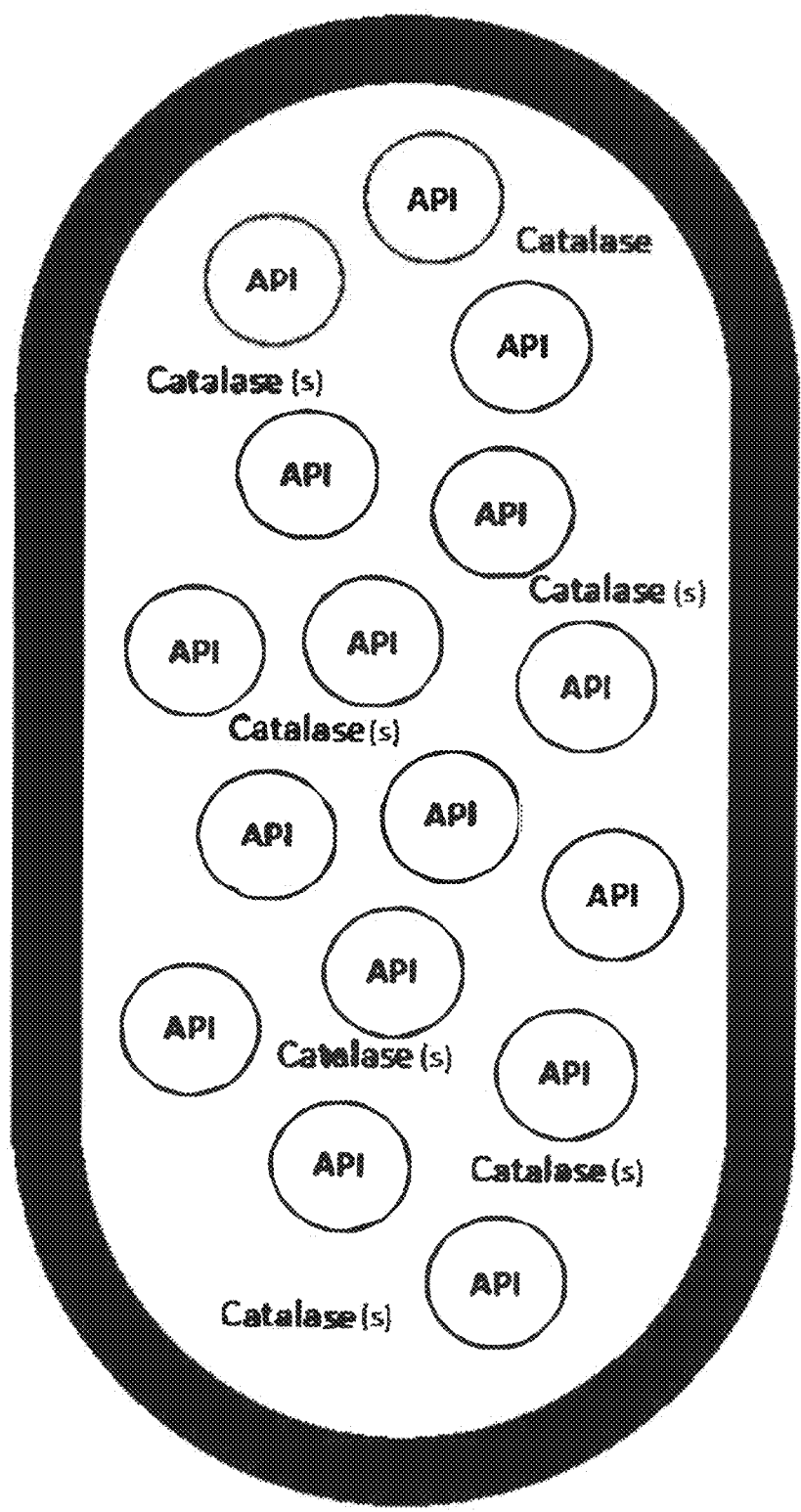
FIG. 1A is a graphical representation of one non-limiting embodiment of a formulation for delivery of oxygen via catalytic release of oxygen from an oxygen prodrug.

Several embodiments of the present disclosure provide an elegant solution to treating anaerobic infections and overcome certain disadvantages of existing therapies.

The intestinal lumen is largely an anaerobic environment. Its oxygen content is complex and variable being a function of how much air is swallowed during food ingestion, how much of that air is transported into the intestine versus eructated, oxygen consumption by intestinal aerobes and facultative anaerobes, and potentially some minimal absorption via intestinal villi. However, while intestinal anaerobes may be forced to endure short bursts of low oxygen partial pressures, the intestinal lumen is predominantly an optimal anaerobic environment for their growth.

This anaerobic environment not only supports the growth of virulent, anaerobic pathogens, but may enhance their virulence via a variety of other ways. In addition to evolving antibiotic resistance of these pathogens, the function of some antibiotics is impaired under anaerobic conditions.

Hypoxia is thought to induce intestinal inflammation. Anaerobic conditions induce pathogen expression of virulence factors and damage tight junctions between host epithelial cells that act as a barrier to invasive infections. Anaerobia can decrease host defense mechanisms.

As disclosed herein, aerobization of the bowel lumen can be used to prevent and treat anaerobic infections as well as non-infectious pathology exacerbated by the hypoxic state of the distal bowel.

Some embodiments of the present disclosure are related to agents, kits, and methods that utilize oxygenation to prevent and/or treat infections in the intestine caused by anaerobic microorganisms. Some embodiments of the present disclosure are related to compositions, kits, and methods that can be utilized to oxygenate the intestinal lumen to prevent and/or treat infections caused by anaerobic bacteria. In some embodiments, the present disclosure is related to compositions, kits, and methods that can be utilized to prevent and/or treat anaerobic bacterial infections of the intestinal lumen by enteric aerobization therapy (EAT).

Several embodiments of the present disclosure overcome one or more concerns of existing oxygenation therapies. For example, hyperbaric oxygen therapy has demonstrated some benefit in the treatment of infections such as gas gangrene, demonstrating both bacteriostatic and bactericidal effects. Hemoglobin is well saturated at normobaric pressures, so the primary mechanism of hyperbaric oxygen therapy is to enhance oxygen delivery via increased dissolved oxygen in the plasma via high partial pressure of oxygen. Though there may be some direct effects on open wounds, administration of hyperbaric oxygen is predominantly via the respiratory system. While research has demonstrated hyperbaric oxygen affects the growth of intestinal bacteria, notably decreasing the growth of obligate anaerobes in mice, hyperbaric oxygen therapy is not used as a therapy for intestinal infections caused by obligate anaerobic pathogens. Besides lack of efficacy against enteric infections, hyperbaric oxygen therapy has limitations for the treatment of other hypoxic enteric diseases. It requires expensive, specialized equipment and so is not readily available to large numbers of patients even in developed nations. It decreases the therapeutic index of oxygen as a drug narrowing the margin between safe and toxic doses. And it does not rapidly change intralumenal oxygen concentration. In some embodiments, some of these issues are mitigated by the use of the agents described herein in conjunction with or instead of hyperbaric oxygen.

Enteric Aerobization Therapy

In several embodiments of the present disclosure, enteric aerobization therapy (EAT) provides one or more agents (e.g., compounds, etc.) that deliver to and/or act as a source of oxygen at a desired location. As used herein, the terms agent and compound may be used interchangeably. In some embodiments, one or more agents that deliver to and/or act as a source of oxygen at an intestinal location or other tissue site in the gastrointestinal tract or elsewhere in the body. In some embodiments, the one or more agents that deliver to and/or act as a source of oxygen at an intestinal location in a controlled manner so as to convert the anaerobic enteric environment to consistently and/or substantially aerobic environment. This can be accomplished via at least two technological methods. In some embodiments, EAT is accomplished via oxygen carrier molecules and oxygen containing mixtures. In some embodiments, EAT is accomplished via oxygen prodrugs or oxygen generating compounds. In some embodiments, EAT is accomplished via a combinations of oxygen carrier molecules and oxygen containing mixtures and oxygen prodrugs or oxygen generating compounds. In some embodiments, the intestinal location can be the lumen, inner wall of the intestine, or both. In some embodiments, the intestine can be small intestine, large intestine, or both. In some embodiments, the intestinal location can be a part of the upper gastrointestinal tract, lower gastrointestinal tract, or both. In one embodiment, multiple locations of the gastrointestinal tract (GI) system are treated.

In some embodiments, the conversion of the anaerobic enteric environment to an aerobic environment is measured by various methods, including measurement of flatus gas composition. In some embodiments, oxygen concentration will be increased by about 20% or more in the enteric environment and/or sufficiently aerobic to provide a therapeutic benefit. In some embodiments, at least 3% oxygen (gas phase) is achieved for 24 hours or more. At least 3-5%, 5-10%, 10-25% oxygen is achieved for at least 12, 18, 24 or 48 hours in several embodiments.

In some embodiments, the conversion of the anaerobic enteric environment of the target site (e.g., intestine) to an aerobic environment is sufficient to inhibit growth, reduce toxicity of the anaerobic bacterial infection or both.

In some embodiments, inhibition of growth and/or reduction of toxicity are measured using a glutamate dehydrogenase assay (which correlates with C diff growth), growth cultures, toxicity assays, ELISA, or other tests.

In some embodiments, conversion of the anaerobic enteric environment of the target site (e.g., intestine) to an aerobic environment results in inhibition of growth to below a threshold. In some embodiments, conversion of the anaerobic enteric environment of the target site (e.g., intestine) to an aerobic environment results in reduction of toxicity to below a threshold. The threshold may be functional and ascertained by a subject's reduction in symptoms. The threshold may be assessed by quantitative and qualitative assessments of microbial growth and activity.

In some embodiments, EAT is accomplished using one or more agents that deliver oxygen and/or act as a source of oxygen such as oxygen carrier molecules and oxygen containing mixtures, including but not limited to, oxygen binding biomolecules (e.g., hemoglobin and/or myoglobin), oxygen cocktails, microemulsions of oxygen gas bubbles, microemulsions of oxygen gas foams, and perfluorocarbons (such as perfluorocarbon oxygen solutions).

In some embodiments, EAT is accomplished via oxygen prodrugs or oxygen generating compounds, including but not limited to, hydrogen peroxides, carbamide peroxide, calcium peroxide, magnesium peroxide, sodium percarbonate, and endoperoxides.

In some embodiments, provided herein are combinations of one or more agents that deliver oxygen and/or act as a source of oxygen. In some embodiments, combinations comprise one or more agents that deliver oxygen and/or act as a source of oxygen and are selected from the group consisting of oxygen carrier molecules and oxygen containing mixtures, including but not limited to, oxygen binding biomolecules (e.g., hemoglobin and/or myoglobin), oxygen cocktails, microemulsions of oxygen gas bubbles, microemulsions of oxygen gas foams, and perfluorocarbons.

In some embodiments, combinations comprise one or more agents that deliver oxygen and/or act as a source of oxygen that potentiate one or more other agents that deliver oxygen and/or act as a source of oxygen. The potentiation can be additive or synergistic. Synergy may also be achieved, in some embodiments, by using the agents described herein and one or more other types of antimicrobial drugs (such as antibiotics).

In some embodiments, synergistic or sustained response to a combination of one or more agents that deliver oxygen and/or act as a source of oxygen is observed. In some embodiments, "combination therapy" is intended to encompass administration of one or more agents that deliver oxygen and/or act as a source of oxygen in a sequential manner, wherein each agent that deliver oxygen and/or act as a source of oxygen is administered at a different time, as well as administration of these agents that deliver oxygen and/or act as a source of oxygen, or at least two agents that deliver oxygen and/or act as a source of oxygen concurrently, or in a substantially simultaneous manner. Simultaneous administration can be accomplished, for example, by administering to the subject a single dosage form, for example, a solution, pill (such as a tablet or caplet) or capsule, having a fixed ratio of each agent that delivers oxygen and/or acts as a source of oxygen or in multiple, single dosage forms for each agent that delivers oxygen and/or acts as a source of oxygen. Sequential or substantially simultaneous administration of each compound/agent that delivers oxygen and/or acts as a source of oxygen can be effected or accomplished by any appropriate route including, but not limited to, oral routes, intravenous routes, intramuscular routes, rectal routes, topical routes, intrathecal routes, intranasal routes, intraocular routes, intraperitoneal routes, and direct absorption through mucous membrane tissues. The formulations and compositions comprising or consisting essentially one, two, three or more agents described herein also include, in some embodiments, excipients, coatings for localized delivery, time release components, stabilizers, and other biologically active or inactive components to facilitate the effect of the agents described in the present disclosure (e.g., enhancing localization, increasing stability, reducing degradation, etc.). In one embodiment, the formulation comprises or consists essentially one or more active agents and one or more inactive agents. For example, in several embodiments, an agent as provided for herein is coated with one or more of an enteric coating, an osmotic coating, and a barrier coating. For example, in several embodiments, an agent as provided for herein is coated with two or more of an enteric coating, an osmotic coating, and a barrier coating. For example, in several embodiments, an agent as provided for herein is coated with an enteric coating, an osmotic coating, and a barrier coating. In several embodiments, the agents that deliver oxygen and/or act as a source of oxygen are administered in combination (either concurrently or sequentially) with a prebiotic composition. In several embodiments, the agents that deliver oxygen and/or act as a source of oxygen are administered in combination (either concurrently or sequentially) with a probiotic composition.

In some embodiments, mixtures of one or more agents that deliver oxygen and/or act as a source of oxygen can also be administered to the patient as a simple mixture or in suitable formulated pharmaceutical compositions. In some embodiments, combination therapy can be achieved by administering two or more agents that deliver oxygen and/or act as a source of oxygen, each of which is formulated and administered separately, or by administering two or more agents that deliver oxygen and/or act as a source of oxygen in a single formulation. Other combinations are also encompassed by combination therapy. For example, two agents that deliver oxygen and/or act as a source of oxygen can be formulated together and administered in conjunction with a separate formulation containing a third compound/agent that deliver oxygen and/or act as a source of oxygen. While the two or more agents that deliver oxygen and/or act as a source of oxygen in the combination therapy can be administered simultaneously, they need not be. For example, administration of a first agent that deliver oxygen and/or act as a source of oxygen (or combination of agents that deliver oxygen and/or act as a source of oxygen) can precede administration of a second agent that deliver oxygen and/or act as a source of oxygen (or combination of agents that deliver oxygen and/or act as a source of oxygen) by minutes, hours, days, or weeks. Thus, the two or more agents that deliver oxygen and/or act as a source of oxygen can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two, three, four or more agents that deliver oxygen and/or act as a source of oxygen used in a combination therapy be present within the patient's body at the same time, this need not be so in other cases. In one embodiment, treatment with the agents described herein are provided on a long-term basis for certain vulnerable patient populations. In several embodiments, the oxygen concentration of tissue (including intestinal tissue) post treatment with the agents described herein is at least 25%, 50%, 75%, 2×, 3-5×, 10× or more as compared to pretreatment. In several embodiments, anaerobic microorganism growth and/or activity is reduced by at least 50% within hours or days post treatment. Although treatment of the GI tract is described herein, other tissue requiring oxygenation may also be treated according to some embodiments.

In several embodiments, the formulation comprises an API (e.g., an oxygen prodrug) at 100 to 3000 mg per dose (e.g., 100 to 200 mg, 150 to 250 mg, 250 to 500 mg, 100 to 500 mg, 500 to 1000 mg, 750 to 1000 mg, 800 to 1200 mg, 1000 to 2000 mg, and overlapping ranges therein) with an optional catalyst at 5 to 10,000 Baker units (e.g., 5 to 25 Baker units, 10 to 100 Baker units, 25 to 50 Baker units, 50 to 150 Baker units, 150 to 300 Baker units, 300 to 750 Baker units, 500 to 1000 Baker units, 1000-2000 baker units/gram of catalyst, 2000-3000 baker units/gram of catalyst, 3000-4000 baker units/gram of catalyst, 4000-5000 baker units/gram of catalyst, 5000-6000 baker units/gram of catalyst, 6000-7000 baker units/gram of catalyst, 7000-8000 baker units/gram of catalyst, 8000-9000 baker units/gram of catalyst, 9000-10000 baker units/gram of catalyst, and overlapping ranges therein). The formulation may be provided once daily, 2-6 times daily or as needed. In some embodiments, the catalyst (such as catalase) is provided in a range of 100 to 2000 mg (e.g., 100 to 500 mg, 500 to 1000 mg, 500 to 1500 mg, 1000 to 2000 mg, and overlapping ranges therein). In some embodiments, the catalyst (such as catalase) is provided in a range of 2500 to 10000 IU (e.g., 2500 to 5000 IU, 5000 to 7500 IU, 7500 to 10000 IU, and overlapping ranges therein).

In several embodiments, the formulation comprises an API (e.g., an oxygen prodrug) at 100 to 3000 mg per dose (e.g., 100 to 200 mg, 150 to 250 mg, 250 to 500 mg, 100 to 500 mg, 500 to 1000 mg, 750 to 1000 mg, 800 to 1200 mg, 1000 to 2000 mg, and overlapping ranges therein). In several embodiments, catalase is provided by a biological material, as provided for herein. In several embodiments, the biological material is provided in an amount similar to that of the prodrug, e.g., 100 to 3000 mg per dose (e.g., 100 to 200 mg, 150 to 250 mg, 250 to 500 mg, 100 to 500 mg, 500 to 1000 mg, 750 to 1000 mg, 800 to 1200 mg, 1000 to 2000 mg, and overlapping ranges therein). In several embodiments, the biological material is provided in a greater amount than the prodrug, for example, 3000-5000 mg (e.g., 3000-3500 mg, 3500-4000 mg, 4000-4500 mg, 4500-5000 mg and overlapping ranges therein). In several embodiments, biological material is present in an amount such that there is an excess of catalase as compared to the prodrug substrate (e.g., 5% in excess, 10% in excess, 25% in excess, 50% in excess, 100% in excess, 200% in excess, or greater (including amounts between those listed)).

In some embodiments, the catalyst (such as catalase) is provided at 10 to 10,000 baker units/gram of catalyst (e.g., 10 to 25 baker units/gram of catalyst, 25 to 50 baker units/gram of catalyst, 50-100 baker units/gram of catalyst, 100-200 baker units/gram of catalyst, 200-300 baker units/gram of catalyst, 300-400 baker units/gram of catalyst, 400-500 baker units/gram of catalyst 500-600 baker units/gram of catalyst, 600-700 baker units/gram of catalyst, 700-800 baker units/gram of catalyst, 800-900 baker units/gram of catalyst, 900-1000 baker units/gram of catalyst, 1000-2000 baker units/gram of catalyst, 2000-3000 baker units/gram of catalyst, 3000-4000 baker units/gram of catalyst, 4000-5000 baker units/gram of catalyst, 5000-6000 baker units/gram of catalyst, 6000-7000 baker units/gram of catalyst, 7000-8000 baker units/gram of catalyst, 8000-9000 baker units/gram of catalyst, 9000-10000 baker units/gram of catalyst, and overlapping ranges therein). One baker unit shall be given its ordinary meaning and shall also refer to the amount of catalase that will decompose 264 mg of hydrogen peroxide under assay conditions of pH 7.0 and 25° C. The ratio of the API to the catalyst (e.g., by weight) in some embodiments is 1:1, 1:2, 1:3, 1:4, 1:10, 1:20, 1:30, 1:40, 1:50, 1:75, 1:100, 1:200, 10:1, 9:1, 8:1, 7:1, 6:1, 5:1, 4:1, 3:1, or 2:1. The formulation may also comprise inactive ingredients such as one or more of the following: acacia gum, rice flour, cellulose, starch, stearates (e.g., magnesium stearate), gelatin, carbonates (e.g., calcium carbonate) and other binders, stabilizers, excipients, and pH balancers. In some embodiments, the starch is instant starch, modified starch or unmodified starch. Non-limiting sourced of starch include corn, potato, rice, wheat and tapioca. In some embodiments, the ratio of the prodrug to inactive ingredients (e.g., by weight) is 1:1, 1:2, 1:3, 1:4, 10:1, 9:1, 8:1, 7:1, 6:1, 5:1, 4:1, 3:1, or 2:1. In some embodiments, the ratio of the prodrug to inactive ingredients (e.g., by volume) is 1:1, 1:2, 1:3, 1:4, 10:1, 9:1, 8:1, 7:1, 6:1, 5:1, 4:1, 3:1, or 2:1. In some embodiments, the ratio of the inactive ingredient to the catalyst (e.g., by weight) is 1:1, 1:2, 1:3, 1:4, 1:5, 1:6, 1:7 or 1:8. In some embodiments, the ratio of the inactive ingredient to the catalyst (e.g., by volume) is 1:1, 1:2, 1:3, 1:4, 1:5, 1:6, 1:7 or 1:8.

The formulation (e.g., supplement) may be provided in solid form as tablets, capsules, caplets, and the like, which may be divided into 2-4 smaller sub-doses to facilitate swallowing. In some embodiments, the formulation may be provided in solid form as multiple capsules within another capsule. In some embodiments, one or more inner capsules contain a prodrug. In some embodiments, the outer capsule encapsulates a catalyst that surrounds one or more inner capsules. In some embodiments, the formulation may be provided in solid form as nested layers of ingredients. In some embodiments, one or more inner coatings encapsulates a prodrug (optionally in tableted form). In some embodiments, an outer coating encapsulates a catalyst that surrounds the prodrug, which is encapsulated in its own coating(s).

In one embodiment, the API comprises at least one of sodium percarbonate and carbamide peroxide and the catalyst comprises catalase. In other embodiments, the API comprises at least one of sodium percarbonate and carbamide peroxide and the catalyst is provided by one or more yeast types. In other embodiments, the API comprises at least one of sodium percarbonate and carbamide peroxide and the catalyst is provided by *Spirulina*. In some embodiments the API comprises at least one of sodium percarbonate and carbamide peroxide and the catalyst is provided by *Chlorella*.

In some embodiments, the prodrug is capable of oxygenating the intestinal region after storage of the oral formulation for at least 20 days (e.g., 20, 25, 30, 35, 40, 45, 50, 55, 60 days, and overlapping ranges therein). In some embodiments, the prodrug is capable of oxygenating the intestinal region after storage of the oral formulation at ~22° C. for at least 5 days.

In some embodiments, the prodrug is capable of oxygenating the intestinal region after storage of the oral formulation at room temperature. In some embodiments, the room temperature can be defined as any temperature that is in between 20° C. and 29° C. (e.g., 20, 21, 22, 23, 24, 25, 26, 27, 28, 29° C., and overlapping ranges therein). In some embodiments, the formulation comprising prodrug and the catalyst are stable (e.g., maintain oxygen producing capacity) with refrigeration of the formulation for at least 20, 25, 30, 35, 40, 45, or more days (including overlapping ranges therein).

In some embodiments, the formulation comprising prodrug and the catalyst are stable (e.g., maintain oxygen producing capacity) without refrigeration of the formulation for at least 0, 1, 2, 5, 7, 9, 10, 12, 15, 17, 20, or more days (including overlapping ranges therein).

In some embodiments, EAT is used to control the growth of gastrointestinal microbiota, gut microbiota, or gut flora. In some embodiments, EAT is used to prevent and/or treat anaerobic infections, including but not limited to, *Clostridioides difficile* infections, foodborne infections (e.g., food poisoning) caused by *Clostridium perfringens*, botulism caused by *Clostridium botulinum, Clostridium butyricum*, and *Clostridium baratii*, cholera caused by *Vibrio cholera*, diarrheagenic *Escherichia coli* infections, *Salmonella enteritidis*, Inflammatory Bowel Disease, and other infections and/or diseases associated with the gastrointestinal tract.

In some embodiments, EAT is used to prevent and/or treat infections that are in anaerobic compartments of the intestinal compartment. In some embodiments, EAT can be used to prevent and/or treat any infection that is any anaerobic compartment of the body.

In some embodiments, EAT is used to prevent and/or treat infections of humans. In some embodiments, EAT is used to prevent and/or treat infections of non-human primates. In some embodiments, EAT is used to prevent and/or treat infections of other animals, including but not limited to, dogs, cats, cattle, sheep, fowl, birds, domestic animals, pets, experimental animals, and/or commercially important animals, and the like.

In some embodiments, any of the formulations described herein can be formulated into one or more extended release and delivery, delayed release and delivery, sustained release and delivery, and/or controlled release and delivery formulations. An oral formulation, in several embodiments, is provided in a solid form (including pills such as tablets and caplets, etc.). Pills may be round, oval, oblong, disc shaped, or other suitable shape for administration and may be partially or fully coated or uncoated. Capsules may contain gel, solid and/or or liquid ingredients. In one embodiment, solid formulations are particularly efficient at oxygen delivery.

In some embodiments, any of the formulations described herein can be formulated into one or more nanoparticle formulations. In some embodiments, the nanoparticles can be one or more nanospheres, nanocylinders, nanoplates, nanoshells, nanorods, nanorices, nanofibers, nanowires, nanopyramids, nanoprisms, nanostars, nanocrescents, nanorings, and nanoantennas. In some embodiments, the dimensions of the nanoparticles can range from about 1 nm to about 100 nm. In some embodiments, the dimensions of the nanoparticles can range from about 100 nm to about 250 nm. In some embodiments, the dimensions of the nanoparticles can range from about 20 nm to about 1000 nm. In some embodiments, the dimensions of the nanoparticles can range from about 4 nm to about 6250 nm. In some embodiments, the dimensions of the nanoparticles is about 1, 5, 10, 20, 30, 40, 50, 60, 70, 80, 90, 100, 200, 300, 400, 500, 750, 1000 nm, or a value within a range defined by any two of the aforementioned values. In some embodiments, the amount of a formulation that can be incorporated within a nanoparticle depends on the size of the nanoparticle. Thus, the greater the size of a nanoparticle, the greater the amount of a formulation that can be incorporated within the nanoparticle.

The route of administration of any of the formulations described herein can be determined by one of ordinary skill in the art based on the circumstances. Several non-limiting routes of administrations are possible including parenteral, subcutaneous, intraarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal.

Therapeutic Uses of Enteric Aerobization Therapy (EAT)

In some embodiments, one or more therapeutic uses of EAT are described herein based on any of the compositions, kits, and methods described herein. In some embodiments, more than one therapeutic use of EAT can be used in combination described herein. In some embodiments, one or more formulations that are used to deliver oxygen via one or more mechanisms are described. Any of the therapeutic uses of EAT can applied based on any of the formulations described herein can be used to deliver oxygen via any of the mechanisms described herein.

*Clostridioides difficile* Infections (CDI)

*Clostridioides difficile* (formerly *Clostridium difficile*) is an endospore-forming, obligately anaerobic pathogen. *C. difficile* is a major cause of nosocomial infection causing antibiotic-associated diarrhea, pseudomembranous colitis, toxic megacolon, sepsis and death. There are an estimated 450,000 cases per year, half of them community acquired, half in seriously ill inpatients resulting in nearly 13,000 deaths annually and billions of dollars in excess healthcare costs.

Patients are predisposed to CDIs when being treated with a broad-spectrum antibiotics which disrupts a healthy microbiome in the body (e.g., the intestine's normal microbiome). Commonly used antibiotics that predispose to CDIs include clindamycin, fluoroquinolones, and cephalosporins, though CDI can manifest as a complication of treatment with any antibiotic. CDIs can be difficult to eradicate because even when successfully treated CDIs often recur. There are only three antibiotics (metronidazole, vancomycin, and fidaxomicin) commonly used to treat CDIs and the success rate for treatment is relatively low. This combination of high morbidity, mortality, economic burden, and poorly effective treatment options has created an urgent demand for better therapeutics.

While many interesting strategies are being employed in the search for novel CDI therapeutics, these strategies can be categorized into traditional therapeutic categories for treating and/or prophylaxis against infection: 1) small molecules targeting *C. difficile* directly or indirectly, such as targeting toxins, inhibiting endospore vegetation; 2) immunotherapy, passive and active, targeting *C. difficile* or its disease-causing toxins; 3) bacteriological, aiming to restore microbiome balance. Patent reviews demonstrate similar strategies, including: 1) anti-*C. difficile* small molecules; 2) passive and active immunotherapy/vaccinations; 3) bacteriological; as well as 4) special diet/nutrients; 5) genetic/molecular biological; 6) phage therapy; and 7) anti-virulent therapy.

EAT offers a benign and effective way of preventing and/or treating CDIs. The active pharmaceutical ingredient (API) is oxygen, a safe molecule with a very high therapeutic index under normobaric conditions. Aerobic conditions are toxic to the vegetative state of *C. difficile* forcing it into its metabolically dormant spore state to survive. *C. difficile* endospores do not cause disease and do not compete with normal colonic flora, allowing the latter its synergistic, protective function.

Importantly, there is no selective pressure for *C. difficile* to develop resistance to oxygen. That is because it is already resistant; it forms endospores to survive oxygen exposure. Endospore-forming *Clostridium* branched from the bacterial evolutionary tree at about the same time as the Great Oxidation Event. Since for 2.3 billion years it has survived a toxic aerobic biosphere by forming non-disease-causing endospores, it is most unlikely for it to evolve an alternate resistance mechanism. Accordingly, several embodiments provide a safe and effective therapy, with no or reduced propensity to select for resistance.

Foodborne Infections (Food Poisoning)

According to the CDC, foodborne infections cause 48 million infections, 128,000 hospitalizations, and 3000 deaths annually. Many of these infections are caused by pathogens in which the anaerobic state of the intestine enhances virulence. Some non-limiting examples are listed below.

*Clostridium perfringens*

*Clostridium perfringens* is an endospore-forming, Gram-positive pathogen that causes an estimated 1 million cases of food poisoning annually in the United States.

While the disease is generally self-limiting, in some embodiments, EAT can be used as a safe, effective, non-antibiotic means of accelerating recovery as well as preventing hospitalizations and death.

In some embodiments, any of the therapeutic uses of EAT can be applied based on any of the formulations described herein to be used to deliver oxygen via any of the mechanisms described herein as a safe, effective, non-antibiotic means of accelerating recovery as well as preventing hospitalizations and death.

Botulism

*Clostridium botulinum, Clostridium butyricum*, and *Clostridium baratii* are causative agents causing botulism. These organisms produce a neurotoxin that is one of the most lethal toxins known. While hospitalization and treatment with antitoxin is the mainstay of therapy, sometimes antibiotics are administered to clear the toxin-producing infection. However, the bacteria can rapidly develop resistance to antibiotics.

In some embodiments, EAT can be used as a replacement and/or supplement to antibiotics. In one embodiment, EAT and antibiotics work synergistically. As a nonlimiting example, EAT may reduce the dose of time period of antibiotics required, which can then in turn reduce the undesired side effects of certain antibiotics.

In some embodiments, any of the therapeutic uses of EAT can be applied based on any of the formulations described herein to be used to deliver oxygen via any of the mechanisms described herein as a replacement and/or supplement to antibiotics.

Cholera

Cholera is caused by the foodborne, facultative anaerobic pathogen, *Vibrio cholerae*. While the disease is rare in the United States, it is a much greater problem in developing nations with poorer sanitation systems. Rehydration is the mainstay of therapy and in severe cases may require parenteral rehydration which is a challenge for many living in developing nations with limited access to healthcare. While *V. cholerae* tolerates oxygen, anaerobic conditions exacerbate its virulence.

In some embodiments, EAT can serve as an affordable adjunctive to maximize onset of efficacy of antibiotic therapy and lessen severity of disease.

In some embodiments, any of the therapeutic uses of EAT can be applied based on any of the formulations described herein can be used to deliver oxygen via any of the mechanisms described herein to serve as an affordable adjunctive to maximize onset of efficacy of antibiotic therapy and lessen severity of disease.

Diarrheagenic *Escherichia coli*

*Escherichia coli*, like *V. cholerae*, is a facultative anaerobe that has many pathogenic strains including those that cause serious foodborne infections.

Non-limiting examples of strains that cause enteric infections include Shiga toxin-producing *E. coli* (STEC) (a.k.a. Verocytotoxin-producing *E. coli* (VTEC) or enterohemorrhagic *E. coli* (EHEC)), enterotoxigenic *E. coli* (ETEC), Enteropathogenic *E. coli* (EPEC), enteroaggregative *E. coli* (EAEC), enteroinvasive *E. coli* (EIEC), and diffusely adherent *E. coli* (DAEC).

Enteric infections caused by these organisms can benefit from EAT because anaerobia is thought to exacerbate virulence.

In some embodiments, any of the therapeutic uses of EAT can be applied based on any of the formulations described herein. Several embodiments can be used to deliver oxygen via any of the mechanisms described herein to render facultative anaerobic strains less virulent and/or avirulent.

Salmonella

The *Salmonella* genus are disease causing facultative anaerobic organisms that is more virulent in anaerobic conditions and may benefit from EAT. In the United States *Salmonella enteritidis* is a significant cause of morbidity and mortality causing 1.35 million infections a year resulting in 26,500 hospitalizations and 420 deaths. *Salmonella Typhi* and Paratyphi are the causative agents of Typhoid fever that infect up to 21 million people globally each year.

In some embodiments, any of the therapeutic uses of EAT can be applied based on any of the formulations described herein can be used to deliver oxygen via any of the mechanisms described herein to render these facultative anaerobic strains less virulent and/or avirulent.

Inflammatory Bowel Disease (IBD)

Inflammatory bowel disease, Crohn's disease and ulcerative colitis, are diseases of chronic inflammation of the gastrointestinal tract. There are about 1.6 million people afflicted with IBD in the United States. Though the causes are unknown, these diseases are not thought to be infectious in etiology. However, mounting evidence suggests that intestinal hypoxia may contribute to the pathogenesis of these diseases.

Thus, in some embodiments, IBD (e.g., one or symptoms or flare ups) can be prevented and/or treated by EAT. In some embodiments, any of the therapeutic uses of EAT can applied based on any of the formulations described herein can be used to deliver oxygen via any of the mechanisms described herein to prevent and/or treat IBD.

Oxygen Carriers

Oxygen Binding Biomolecules

Hemoglobins and myoglobin are the two most predominant oxygen carrying biomolecules known. Myoglobin is a component of major constituent of red meat and can be biochemically isolated from meat. Animal hemoglobin is more readily available for biochemical isolation from animal processing plants. Another route of production could be achieved via cloning and expression bioengineering.

Myoglobin and hemoglobin bind oxygen well in solution. In some embodiments, formulations of myoglobin and/or hemoglobin are administered to patients in the form of solutions. Other hemeproteins are also provided in some embodiments. In one embodiment, leghemoglobin is used. In some embodiments (e.g., using leghemoglobin), drinks and supplements are provided with additional flavoring.

In some embodiments, formulations are provided as solutions that minimize and/or avoid denaturing by gastric acid. In some embodiments, formulations are provided as solutions that minimize and/or avoid uncontrolled release of oxygen prematurely before the desired dose reaches its target (e.g., intestinal target). One, two or more hemeproteins may be used.

In some embodiments, a lyophilized formulation is provided. In some embodiments, hemeprotein is lyophilized to be formulated and encapsulated into a formulation that protects the hemeprotein from, for example, gastric acids when administered orally. In some embodiments, the hemeprotein is lyophilized in a manner that is cost effective and avoids loss of oxygen in vacuum during lyophilization. One, two or more hemeproteins may be used.

Hemoglobin and myoglobin bind oxygen very tightly, the former especially so in the absence 2,3-bisphosphoglycerate (2,3DPG) which is required in millimolar concentrations for good release of oxygen at physiological pH. In some embodiments hemoglobin (or other hemeproteins) are formulated with 2,3DPB. In some embodiments, oxygen is released as the hemeprotein (such as myoglobin and/or hemoglobin) is digested.

In some embodiments, one or more hemeproteins are used to deliver oxygen in any of the formulations for any of the therapeutic uses of EAT described herein. In some embodiments, one or more formulations are used to deliver oxygen via hemoglobin, myoglobin, leghemoglobin or other hemeprotein. In some embodiments, one or more formulations are used to deliver oxygen via a combination of one, two or more hemeproteins and at least one digestive enzyme, such as proteases (e.g., trypsin, chymotrypsin, carboxy peptidases, etc.). Such enzymes, according to one embodiment, accelerate or otherwise control the release of oxygen.

In some embodiments of the formulations, hemeproteins are formulated such that the occurrence of digestive products of the hemeprotein in the feces is avoided in order to avoid false indications of gastrointestinal bleeding and/or interfere with an assessment for bleeding in the gastrointestinal tract in complicated hospitalized patients.

In some embodiments of the formulations, hemeproteins are formulated such that they have an enhanced oxygen binding capacity available for delivery to the target site (e.g., intestine). In some embodiments of the formulations, the enhanced binding capacity of the hemeprotein allows for small doses to be used for delivering therapeutic doses of oxygen, for example, approximately 0.25 mL to 50 mL of gaseous oxygen per 1-gram dry weight hemeprotein. In some embodiments of the formulations, about 0.25-2, 2-5, 5-10, 10-25, or 25-50 mL of gaseous oxygen per 1-gram dry weight hemeprotein is delivered, or a value within a range defined by any two of the aforementioned values.

Oxygen Cocktails

Oxygen cocktails are microemulsions of oxygen gas bubbles (foams) that are administered orally. In some embodiments a composition comprising microemulsions of oxygen gas bubbles (foams) is used for EAT.

In some embodiments, oxygen cocktails are used to deliver oxygen in any of the formulations for any of the therapeutic uses of EAT described herein. In some embodiments of the formulation, oxygen cocktails are formulated such that the loss of oxygen via eructation is reduced and/or avoided. In some embodiments of the formulation, oxygen cocktails are formulated such that they are not stable for packaging and or mass distribution, and therefore are formulated or packaged as separate components that can be combined to form the oxygen cocktail by the person administering the formulation.

Perfluorocarbons

Perfluorocarbons (PFC) large enough not to act as anesthetics have been tested as to enhance oxygen delivery via plasma. These compounds, in some embodiments, dissolve oxygen well with an estimated capacity of 30-40 ml of gaseous oxygen per 100 ml of PFC. Some PFC formulations have been FDA and EMEA approved as oxygen carriers. One PFC has been FDA approved for use as contrast or imaging agent (e.g., an intestinal radiological contrast agent). These compounds are relatively inexpensive to manufacture and are very safe, though they do have the downside of cause some fecal leakage. These compounds could be formulated and packaged in gas-tight pouches for oral administration.

In some embodiments, perfluorocarbon is used to deliver oxygen in any of the formulations for any of the therapeutic uses of EAT described herein. In some embodiments, the formulation comprises perfluorocarbons. In some embodiments, the formulation comprising perfluorocarbons have an oxygen capacity of about 30 mL to about 40 mL of gaseous oxygen per 100 mL of PFC. In some embodiments, approximately 0.25 mL to 50 ml of gaseous oxygen is delivered. In some embodiments, the formulation comprising perfluorocarbons are formulated such that loss of oxygen due to eructation and off-gassing in the hypoxic stomach is reduced and/or avoided, thus providing a controlled delivery of oxygen to the target site (e.g., intestine).

Oxygen Prodrugs

Prodrugs are a well-known strategy of delivering drugs to their targets. Oxygen generating metal-peroxide salts and hydrogen peroxide complexes are well known in the food, bioremediation, cosmetics, and pharmaceutical industries. However, applicant is unaware of the formulations and methods of delivery described herein to effectively deliver oxygen (e.g., enterically) for the purposes disclosed herein.

In some embodiments, oxygen generating metal-peroxide salts and/or hydrogen peroxide complexes are used to deliver oxygen in any of the formulations for any of the therapeutic uses of EAT described herein. In some embodiments, oxygen generating metal-peroxide salts and/or hydrogen peroxide complexes are in the solid state. In some embodiments, oxygen generating metal-peroxide salts and/or hydrogen peroxide complexes are in the liquid state. In some embodiments, oxygen generating metal-peroxide salts and/or hydrogen peroxide complexes are in the semi-solid state. In some embodiments, oxygen generating metal-peroxide salts and/or hydrogen peroxide complexes are formulated and encapsulated using known technologies to remain unaffected by gastric acid and release oxygen in the target site (e.g., intestinal lumen).

In some embodiments, agents described herein (e.g., oxygen generating metal-peroxide salts and/or hydrogen peroxide complexes) are co-formulated with antibiotics. In one embodiment, instead of in addition to co-formulations, such antibiotics are instructed for administration before, after or simultaneously with the agents described herein. Non-limiting examples of antibiotics include penicillins, for example, phenoxymethylpenicillin, flucloxacillin and amoxicillin, cephalosporins, for example, cefaclor, cefadroxil and cephalexin, Tetracyclines, for example, tetracycline, doxycycline and lymecycline, aminoglycosides, for example, gentamicin and tobramycin, macrolides, for example, erythromycin, azithromycin and clarithromycin, clindamycin, sulfonamides and trimethoprim, for example, co-trimoxazole, Metronidazole and tinidazole, Quinolones, for example, ciprofloxacin, levofloxacin and norfloxacin, and nitrofurantoin. In several embodiments, the compositions and formulations described herein exclude tannins. In one embodiment, the compositions and formulations described herein exclude one or more of the following: gallic acid, epigallic acid, ellagitannin, punicalagin, tannic acid, and pseudotannins. In one embodiment, the compositions and formulations described herein exclude water soluble tannins. In several embodiments, the compositions and formulations described herein exclude phenolics, for example, polyphenols.

In some embodiments, oxygen generating metal-peroxide salts and/or hydrogen peroxide complexes are co-formulated with one or more of antibiotics, anthelmintics, antifungals, antimalarials, antiprotozoals, antivirals, prebiotics, and probiotics. In one embodiment, instead of in addition to co-formulations, such antibiotics are instructed for administration before, after or simultaneously with the agents described herein. In several embodiments, the agents that deliver oxygen and/or act as a source of oxygen are administered in combination (either concurrently or sequentially) with a prebiotic composition. In several embodiments, the agents that deliver oxygen and/or act as a source of oxygen are administered in combination (either concurrently or sequentially) with a probiotic composition.

For example, clindamycin is a broad-spectrum antibiotic on the WHO List of Essential Medicines that is useful in treating some infections caused by community acquired MRSA and in combination with quinine for treating malaria. Though *C. difficile*-associated diarrhea, including fatal colitis, can result from treatment with any antibiotic, clindamycin administration is more strongly associated with the development of CDIs and carries an FDA boxed warning.

The rate of conversion of peroxide containing prodrugs to oxygen can be controlled via the use of catalysts. The catalyst accelerates the decomposition of hydrogen peroxide into water and oxygen via disproportionation reaction. There are many known catalysts for this reaction including, but not limited to iodide, catalase, manganese dioxide, iron (III), silver, dichromate (Equation 1).

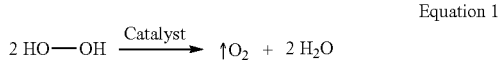

$$2\,HO-OH \xrightarrow{\text{Catalyst}} \uparrow O_2 + 2\,H_2O \qquad \text{Equation 1}$$

In some embodiments, oxygen generating metal-peroxide salts and/or hydrogen peroxide complexes can be co-formulated with one or more catalysts in order to achieve an enhanced rate of conversion to oxygen and/or to achieve a sustained rate of conversion to oxygen.

The rate of these reactions and their release of oxygen can be further regulated by controlling solubility via known state of the art modified- (e.g., extended or sustained) release methods. In some embodiments, oxygen generating metal-peroxide salts and/or hydrogen peroxide complexes can be co-formulated with one or more ingredients that allow for extended release and delivery, sustained release and delivery, and/or controlled release and delivery of the oxygen, for example, formulating the oxygen generating metal-peroxide salts and/or hydrogen peroxide complexes in nanoparticle formulations.

Besides controlling the rate of oxygen release, catalytic conversion mitigates against absorption of hydrogen peroxide, a reactive oxygen species (ROS) systemically by ensuring complete conversion to oxygen. Thus, catalysts are provided in several embodiments.

Potassium iodide, included in the WHO List of Essential Medicines, is available over the counter and is used for many different applications such as an expectorant dosed up to 600 mg four times daily in an adult. It is also used as a thyroid block during accidental nuclear exposure, thyroid gland protection in Graves' disease, and to treat cutaneous/lymphocutaneous Sporotrichosis. Iodide is a safe drug and is absorbed systemically via the intestinal sodium iodide symporter. In some embodiments, iodide is used to control the rate of conversion of peroxide containing prodrugs to oxygen. In some embodiments, any absorption of iodide before peroxide to oxygen conversion is complete is mitigated by formulating the iodide for extended release and delivery, sustained release and delivery, and/or controlled release and delivery of the oxygen, for example, by controlling solubility and/or encapsulation into a hydrogel that retards diffusion. In some embodiments, iodides can be co-formulated with one or more ingredients that allow for extended release and delivery, sustained release and delivery, and/or controlled release and delivery of the oxygen, for example, formulating the iodides in nanoparticle formulations.

Catalase is a natural enzyme produced for and used by the food industry to remove hydrogen peroxide after equipment cleaning and to remove hydrogen peroxide from milk prior to manufacturing cheese. It is also used to remove hydrogen peroxide after contact lens cleaning and disinfecting. The enzyme is highly efficient and is diffusion rate limited.

In some embodiments, catalase or other catalyst is used to control the rate of conversion of peroxide containing prodrugs to oxygen. In some embodiments, the degradation of catalase before peroxide to oxygen conversion is completely mitigated by formulating the catalase for extended release and delivery, sustained release and delivery, and/or controlled release and delivery of the oxygen, for example, by controlling degradation and/or encapsulation into a hydrogel that retards degradation, or by formulating the catalase in nanoparticle formulations.

In some embodiments, the degradation of a catalyst (such as catalase) before peroxide to oxygen degradation is complete is mitigated by formulating the catalyst (such as catalase) within a dialysis or osmotic membrane coated capsule or tablet. The pore size of this dialysis membrane is of sufficient size to allow small molecules like water, electrolyte, certain solutes and oxygen to greatly diffuse across the membrane, but small enough to prevent catalase from diffusing out of the capsule or tablet while also preventing digestive enzymes from diffusing into the capsule or tablet. In some embodiments, the catalase is provided within a membrane or other coating that permits water, electrolyte, solutes and oxygen to diffuse out, but prevents the majority of catalase from diffusing out (while also preventing digestive enzymes from diffusing in). The membrane or coating may be provided in a single layer or multiple layers, and may be made from one, two, three or more of the following: functionalized cellulose acetates, cellulose diacetates, cellulose triacetates, cellulose proprionates, cellulose acetate butyrates with varying degrees of substitution. Other polymers include but are not limited to cellulose acetate acetoacetate, cellulose chloroacetate, cellulose acetate furoate, and dimethoxyethyl cellulose acetate. The catalyst, the API or both may be encapsulated, coated or otherwise formulated within means of controlling or regulating diffusion. In several embodiments, the catalyst and API (or oxygen prodrug) are individually coated. For example, in several embodiments, an agent as provided for herein comprising an API (or oxygen prodrug) and a catalyst can comprise multiple layers of the various components, with a coating between each layer. See, for example FIG. 1B. In this non-limiting embodiment, the agent comprises an internal region of sodium carbonate hydrogen peroxide, which is a precursor to oxygen. This region is coated with a barrier coating, which separates it from an enzyme that will act on the sodium carbonate hydrogen peroxide to generate oxygen. In this embodiment, the enzyme comprises catalase. The enzyme is separated from an external enteric coating by an osmotic coating. In several embodiments, the oxygen producing agent as provided for herein (for example, granules contained within a capsule) is coated with one, two or more of an enteric coating, an osmotic coating, and a barrier coating. For example, in several embodiments, an agent as provided for herein is coated an enteric coating, an osmotic coating, and a barrier coating. In several embodiments wherein the agent is contained within a capsule, the capsule may also be coated with one or more coatings, as provided for herein.

Figure 11:
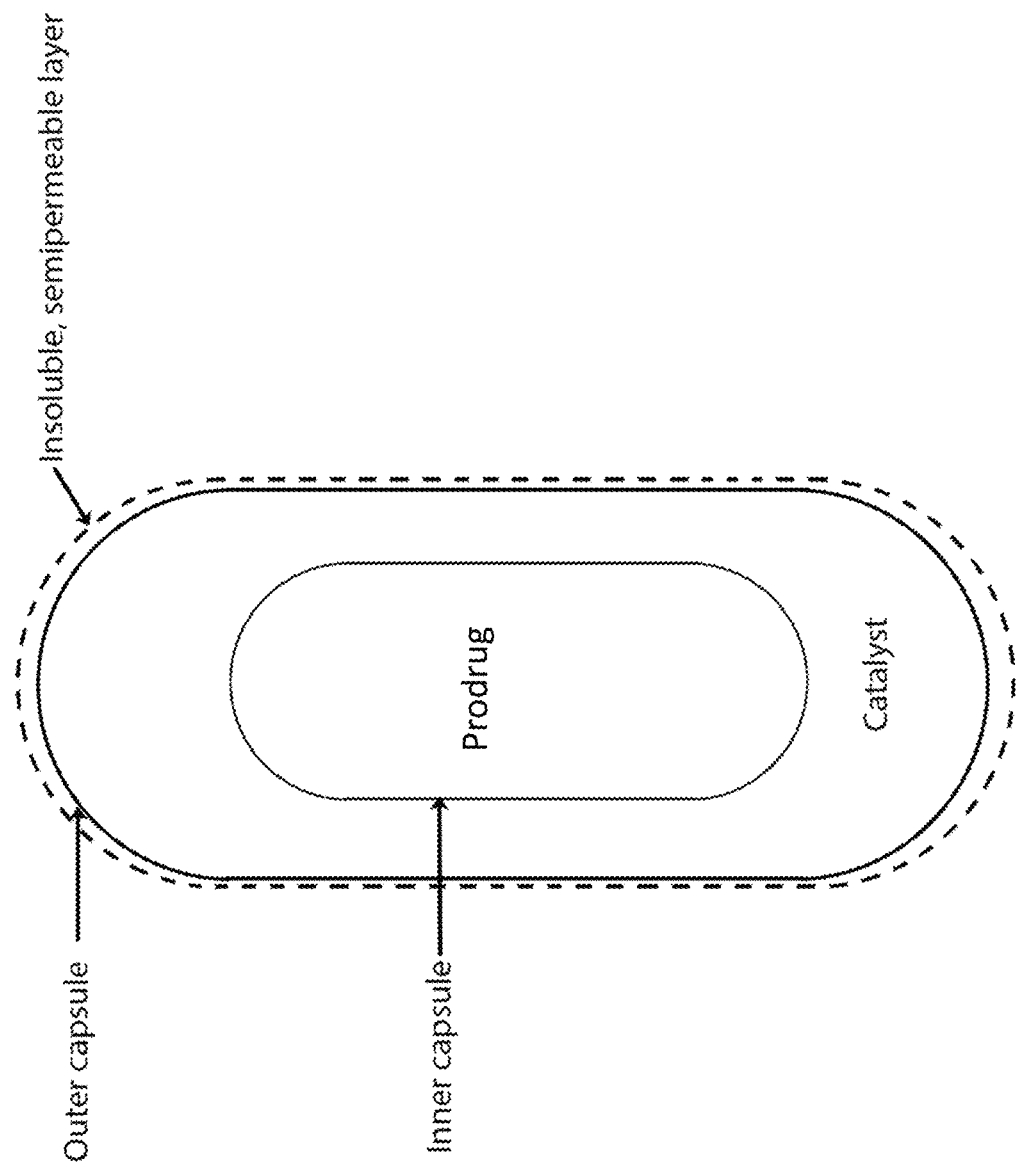
FIG. 11 depicts a non-limiting schematic structure of a capsule-in-a-capsule device (also referred to as coating within a coating).
Figure 12:
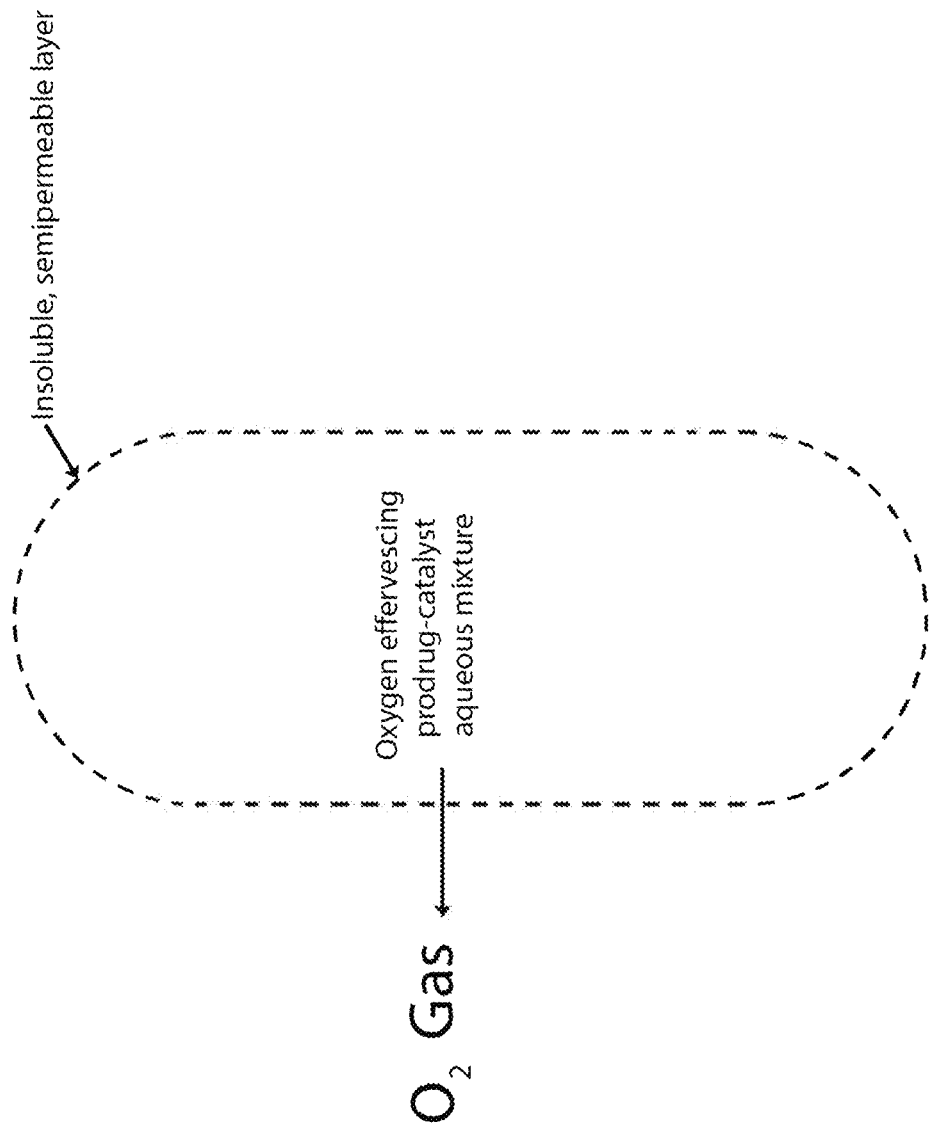
FIG. 12 depicts a non-limiting schematic structure of an activated capsule-in-a-capsule in an environment where the inner and outer capsules have dissolved, such as the higher pH of the small intestine or colon.

In some embodiments, an agent as provided for herein comprising an API (or oxygen prodrug) and a catalyst can be provided as a capsule-in-a-capsule device as depicted in FIG. 11. In this non-limiting embodiment, an API (or oxygen prodrug, preferably sodium percarbonate or percarbamide), is contained within at least one inner capsule and is prevented from physical contact with the catalyst in the outer capsule. The outer capsule encapsulates the catalyst. In the intestines or colon, with their higher resident pH as compared to the stomach, the soluble capsule, enteric coating or other controlled release coatings are dissolved. In some embodiments, the insoluble semipermeable membrane remains intact allowing water to enter the device due to osmotic gradient, dissolving the catalyst (e.g., yeast, catalase) and oxygen prodrug (e.g., sodium percarbonate or percarbamide) initiating the catalytic conversion of hydrogen peroxide to water and oxygen. The oxygen then diffuses out of the device across the insoluble semipermeable membrane as illustrated, for example, in FIG. 12.

Figure 13:
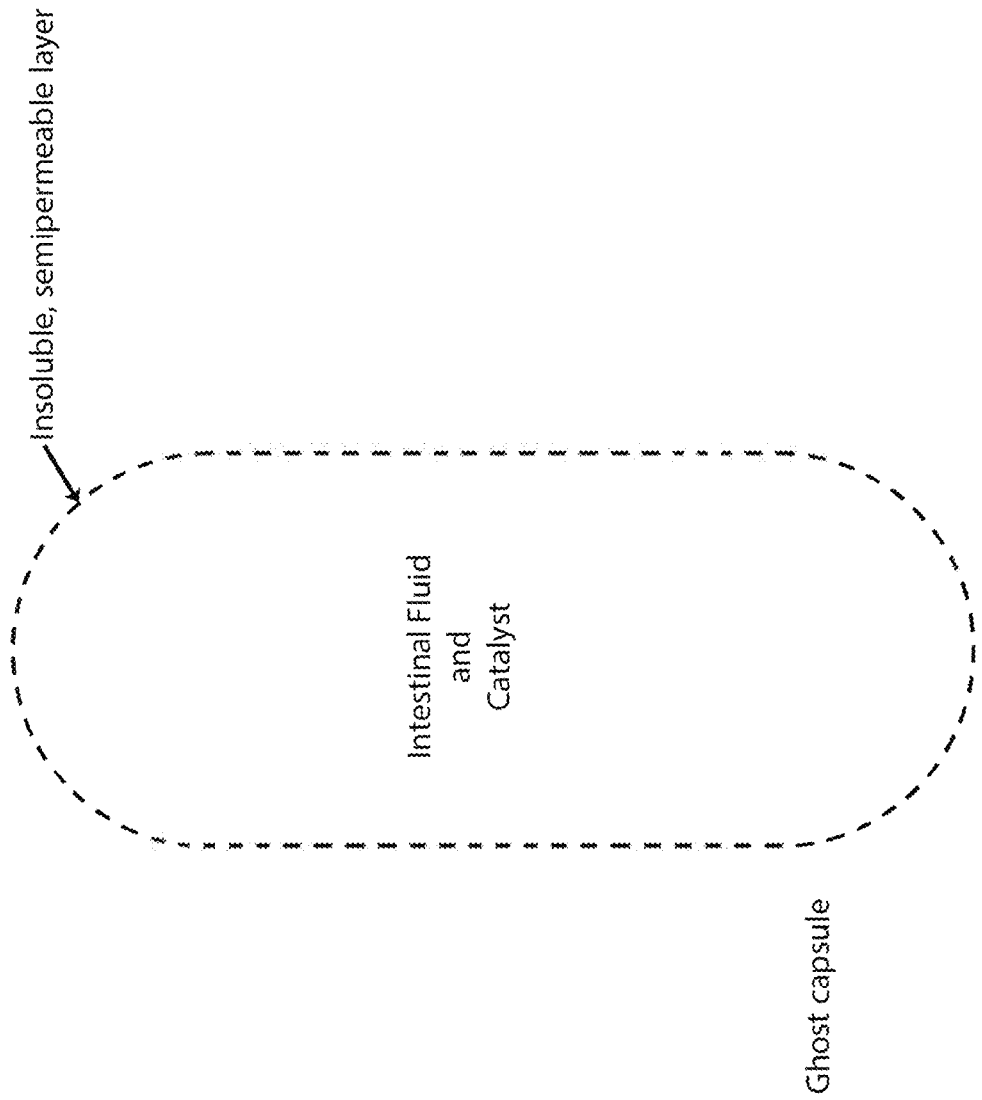
FIG. 13 depicts a non-limiting schematic showing a spent device after all the prodrug has been converted to oxygen and water.

In some embodiments, after all the hydrogen peroxide is converted to oxygen and water, the sodium carbonate and oxygen diffuses away leaving just the entrapped catalyst (if any) within the device dissolved or suspended in equilibrated intestinal fluid as illustrated, for example, in FIG. 13. In some embodiments, the spent shell is eliminated via defecation. In some embodiments, the spent shell is known as a ghost capsule or ghost tablet.

In some embodiments, yeast, catalase or other catalyst surrounds the inner capsule. In some embodiments, the amount of catalyst provided in the outer capsule or tablet is provided in an amount that is sufficient to control the rate of conversion of peroxide containing prodrugs to oxygen. In other embodiments, the amount of catalyst provided in the outer capsule or tablet is provided in an excess amount to control the rate of conversion of peroxide containing prodrugs to oxygen.

In some embodiments, the catalyst is provided as a dry powder. In other embodiments, the catalyst is provided as a suspension. In some embodiments, the catalyst is provided as a solution. The contents of the inner capsule are physically separated from the contents of the outer capsule (or coating) by the inner capsule (or coating). The physical separation of contents of inner capsule and outer capsule stabilizes the formulation by preventing premature conversion of oxygen prodrug.

In some embodiments, the inner and outer capsules are intrinsically enteric. In few embodiments, the inner and outer capsules are covered by an enteric coating using excipients known to those skilled in the art to prevent dissolution in the acidic environment of the stomach. In some embodiments, the inner and/or outer capsule(s) is coated with a controlled release coating. In several embodiments, the oxygen producing agent as provided for herein (for example, capsule-in-a-capsule) is coated with one, two or more of an enteric coating and a controlled release coating. It shall be understood that embodiments reference a capsule could be performed with a coating (e.g., an applied coating rather than a pre-formed shape) and vice versa.

In some embodiments, the outer capsule is coated with a dialysis or osmotic membrane. The pore size of this membrane is of sufficient size to allow small molecules like water, electrolyte, certain solutes and oxygen to greatly diffuse across the membrane, but small enough to prevent catalase, yeast or macromolecules from diffusing out of the capsule.

In some embodiments, an agent comprising an API (or oxygen prodrug) is compressed into a capsule form followed by one, two or more coatings of enteric and controlled layers. In some embodiments, the inner capsule is coated with an enteric layer first followed by a controlled layer. In other embodiments, the inner capsule is coated with a controlled layer first followed by an enteric layer. The coated inner capsule is encased in an outer capsule containing the catalyst. In some embodiments, the outer capsule is coated with one, two or more of an enteric coating and a semipermeable coating. In some embodiments, the outer capsule is coated with an enteric layer followed by a semipermeable layer. In some embodiments, the outer capsule is coated with a semipermeable layer followed by an enteric layer.

In some embodiments, the enteric coating comprises a gelatin capsule. In some embodiments, the gelatin is bovine, porcine, or combinations thereof. In some embodiments, the enteric coating comprises agar-agar, starch or carrageenan. In other embodiments, the enteric coating is made of hydroxypropyl methylcellulose, microcrystalline cellulose or other water soluble/dispersible polymers. In some embodiments, the enteric coating comprises hydroxypropyl methylcellulose phthalate (HPMCP), polyvinyl acetate phthalate, diethyl phthalate, and/or cellulose acetate phthalate.

In some embodiments, the semipermeable coating comprises cellulose acetate, or similar or equivalent suitable polymers or combinations thereof.

Catalysts

Manganese dioxide is an insoluble heterologous peroxide to oxygen catalyst. Manganese dioxide has a low toxicity and may be safe at catalytic concentrations. This catalyst will not be digested and has poor bioavailability, making it an attractive formulation candidate. In addition to catalysis, manganese dioxide may have other beneficial effects on oxygen production.

In some embodiments, manganese dioxide is used to control the rate of conversion of peroxide containing prodrugs to oxygen. In some embodiments, manganese dioxide is provided in a mixture of crystalline structures. In some embodiments, one or more of the mixtures of manganese dioxide crystalline structures catalyzes the peroxide to oxygen reaction. In some embodiments, the mixture of manganese dioxide is enriched for crystalline structures that most efficiently catalyze the peroxide to oxygen reaction.

Another heterogeneous catalysis is metallic silver which is commercially available in powder form. Silver (0) has a low toxicity in low concentrations for short periods of time.

In some embodiments, metallic silver is used to control the rate of conversion of peroxide containing prodrugs to oxygen. In some embodiments of a formulation, metallic silver is formulated in catalytic quantities to achieve catalyzes the peroxide to oxygen conversion.

Ferric iron likewise catalyzes the conversion of hydrogen peroxide to oxygen. Ferrous iron is oxidized by hydrogen peroxide to catalytically active ferric iron, so either oxidation state can be used for formulation.

In some embodiments, ferric or ferrous iron is used to control the rate of conversion of peroxide containing prodrugs to oxygen. In some embodiments, formulation comprising ferric ions, ferrous ions, or both are formulated such that any transient formation of hydroxyl radicals and other reactive oxygen species are minimized and/or avoided.

In some embodiments, at least one single-celled microorganism is used to catalyze the conversion of peroxide to oxygen. In some embodiments, the single-celled microorganism comprises catalase that catalyzes the conversion of peroxide to oxygen. In other embodiments, the single-celled microorganism comprises iodide, manganese dioxide, iron (III), silver or dichromate that can catalyze the peroxide to oxygen.

In some embodiments, the single-celled microorganism is yeast. In some embodiments, the yeast is a Baker's yeast. In some embodiments, the yeast is selected from *Saccharomyces cerevisiae, Saccharomyces exiguous, Saccharomyces eubayanus, Saccharomyces pastorianus, Schizosaccharomyces pombe*, and combinations thereof. In some embodiments the single-celled microorganism is *Chlorella*. In some embodiments, the *Chlorella* is selected from *Chlorella pyrenoidosa, Chlorella vulgaris, Chlorella regularis, Chrolla protothecoides, Chlorella saccharophila*, and combinations thereof. In some embodiments the single-celled microorganism is *Spirulina*. In some embodiments, the *Spirulina* is selected from *Arthrospira platensis, Arthrospira fusiformis, Arthrospira* maxima, and combinations thereof. Combinations of one or more of the microorganisms disclosed herein may be used, depending on the embodiment.

Hydrogen Peroxides

1. Carbamide Peroxide

Carbamide peroxide (a.k.a. artizone, urea hydrogen peroxide, hydrogen peroxide urea, UHP, Hyperol, percarbamide) is a crystalline white solid hydrogen peroxide-urea complex ($CH_6N_2O_3$) that is available without a prescription for topical applications including ear wax removal, oral wound disinfectant, and tooth whitening. It is inexpensive and readily available in bulk quantities. This prodrug is composed of a weak base, urea, and a weak acid, hydrogen peroxide, so in some embodiments the formulation does not include an additional buffer, relying instead on the intrinsic buffering capacity of the intestinal fluid. Buffers are used in some embodiments. Urea is used topically in dermatological medications and is given orally in the urea breath test for *H. pylori*.

Urea is a natural product found in human blood at normal concentration up to 7 mmol/L and is classified by the FDA as a medical food use for the treatment of hyponatremia administered in quantities up to 60 g daily. Without being limited to any particular theory, the yield for conversion is 119 mL gaseous oxygen per gram carbamide peroxide at standard temperature and pressure (STP).

In some embodiments, carbamide peroxide/urea are used to deliver oxygen in any of the formulations for any of the therapeutic uses of EAT described herein. In some embodiments, formulations comprising carbamide peroxide/urea deliver a blood urea concentration of about 10-100 mmol/L. In some embodiments, formulations comprising carbamide peroxide/urea provide about 120 mL gaseous oxygen per gram carbamide peroxide at standard temperature and pressure (STP). In some embodiments, formulations comprising carbamide peroxide/urea deliver a blood urea concentration of about 0.35 mmol/L to about 3.5 mmol/L. In some embodiments, formulations comprising carbamide peroxide/urea deliver a blood urea concentration of about 3.5 mmol/L to about 100 mmol/L. In some embodiments, formulations comprising carbamide peroxide/urea deliver a blood urea concentration of about 0.35 mmol/L to about 100 mmol/L. In some embodiments, formulations comprising carbamide peroxide/urea provide about 12 mL to about 60 mL gaseous oxygen per gram carbamide peroxide at STP. In some embodiments, formulations comprising carbamide peroxide/urea provide about 60 mL to about 120 gaseous oxygen per gram carbamide peroxide at STP. In some embodiments, formulations comprising carbamide peroxide/urea provide about 12 mL to about 120 gaseous oxygen per gram carbamide peroxide at STP. In some embodiments, urea is provided at doses of 1-25 grams per day (e.g., 1-3, 3-5, 5-10 grams) and may be provided once daily or multiple times daily.

2. Calcium Peroxide

Calcium peroxide ($CaO_2$) is a crystalline solid used in the food industry as a flour bleaching agent, dough improving agent, and treatment of rice seeds prior to sowing. It is also used as an oxygenating agent in aquaculture, environmental bioremediation, and has been studied for use in bioengineering. Upon contact with water it decomposes into oxygen, water, and hydrogen peroxide. The ratio of products and rate of reaction heavily dependent on pH.

Calcium peroxide is inexpensive, manufactured on an industrial scale, and is readily available. Calcium peroxide preparations typically contain 25% calcium hydroxide.

In some embodiments, formulations comprising calcium peroxide preparations are formulated with buffer salts for optimal therapeutic value and/or to avoid the potential development of milk alkali syndrome (hypercalcemic metabolic alkalosis). In one embodiment, other additives may be included to reduce calcium hydroxide as a contaminant.

Without being limited to any particular theory, one gram of 75% calcium peroxide can deliver 117 mL gaseous oxygen at STP.

Calcium hydroxide is used in many food preparation processes including but not limited to pickling, baking, Chinese preserved eggs, hominy production. Calcium included in the WHO Essential Medicines List.

In some embodiments, calcium peroxide preparations are used to deliver oxygen in any of the formulations for any of the therapeutic uses of EAT described herein. In some embodiments, formulations comprising calcium peroxide preparations deliver about 120 mL gaseous oxygen per gram of 75% calcium peroxide at STP. In some embodiments, formulations comprising calcium peroxide preparations deliver about 12 mL gaseous to about 60 mL oxygen per gram of 75% calcium peroxide at STP. In some embodiments, formulations comprising calcium peroxide preparations deliver about 60 mL gaseous to about 120 mL oxygen per gram of 75% calcium peroxide at STP. In some embodiments, formulations comprising calcium peroxide preparations deliver about 12 mL gaseous to about 120 mL oxygen per gram of 75% calcium peroxide at STP.

3. Magnesium Peroxide

Magnesium peroxide ($MgO_2$) is similar in chemical properties to calcium peroxide. It is used as an oxygen generator in bioremediation applications. Like calcium, magnesium is a natural ion essential for normal human health.

Without being limited by any particular theory, one gram of 99% pure magnesium peroxide capable of delivering 199 mL gaseous oxygen at STP.

In some embodiments, magnesium peroxide is used to deliver oxygen in any of the formulations for any of the therapeutic uses of EAT described herein. In some embodiments, formulations comprising magnesium peroxide deliver about 40 mL to about 1000 mL of peroxide per one gram of 99% pure $MgO_2$ at STP. In some embodiments, formulations comprising magnesium peroxide deliver about 40 mL to about 150 ml of peroxide per one gram of 99% pure $MgO_2$ at STP. In some embodiments, formulations comprising magnesium peroxide deliver about 150 mL to about 750 ml of peroxide per one gram of 99% pure $MgO_2$ at STP. In some embodiments, formulations comprising magnesium peroxide deliver about 650 mL to about 1050 mL of peroxide per one gram of 99% pure $MgO_2$ at STP.

4. Sodium Percarbonate

Without being limited to any particular theory, one gram of solid sodium percarbonate ($Na_2CO_3 \cdot 1.5\ H_2O_2$) can deliver 107 mL oxygen gas at STP. It is inexpensive and manufactured in industrial scale. It is used in laundry and dishwashing detergents, deodorants, antiseptics and water purification (e.g., household purposes). According to several embodiments, potassium percarbonate is manufactured and used when sodium load from dosing is to be avoided. For example, in one embodiment, substitution of potassium carbonate for sodium carbonate in the sodium percarbonate synthesis would make potassium percarbonate (where low sodium options are desired). Bicarbonate is the majoring buffering system in the human blood stream so the carbonate component will be quite safe as excess will be exhaled from the lungs as carbon dioxide.

In some embodiments, sodium percarbonate is used to deliver oxygen in any of the formulations for any of the therapeutic uses of EAT described herein. In some embodiments, formulations deliver about 10 mL to about 1000 mL oxygen gas per one gram of solid $Na2CO3 \cdot 1.5\ H2O2$ at STP.

In some embodiments, formulations comprising $Na_2CO_3 \cdot 1.5\ H_2O_2$ deliver about 50 mL to about 200 mL oxygen gas per one gram of solid $Na_2CO_3 \cdot 1.5\ H_2O_2$ at STP. In some embodiments, formulations comprising $Na_2CO_3 \cdot 1.5\ H_2O_2$ deliver about 150 mL to about 600 mL oxygen gas per one gram of solid $Na_2CO_3 \cdot 1.5\ H_2O_2$ at STP. In some embodiments, formulations comprising $Na_2CO_3 \cdot 1.5\ H_2O_2$ deliver about 550 mL to about 1050 mL oxygen gas per one gram of solid $Na_2CO_3 \cdot 1.5\ H_2O_2$ at STP.

Table 1 provides a non-limiting example of the components of an oxygen generating composition as provided for herein. This non-limiting embodiment represents a configuration in which each granule of a capsule is coated individually with an enteric coating, a barrier coating and an osmotic coating.

TABLE 1

Coated Granules

| Component/Purpose | Amount per gram | Amount per unit |
|---|---|---|
| Precursor to the Active Ingredient | 500-600 mg | 200-300 mg |
| Binder and Barrier Layer for Pellet Core | 60-70 mg | 25-35 mg |
| Activator | 10-20 mg | 3-12 mg |
| Binder and Coating for Pellet Outer Layer | 1-8 mg | 1-8 mg |
| Sustained Release Coating | 20-30 mg | 10-20 mg |
| Dispersant | 20-30 mg | 10-20 mg |
| Enteric Coating | 200-300 g | 100-200 mg |
| Glidant and Plasticizer | 40-50 mg | 15-30 mg |
| Capsule Shell | N/A | 1 ea |

Endoperoxides

Endoperoxides are bicyclo organic peroxide compounds that release oxygen via retro Diels-Alder reactions.

Synthetic routes are known, but will necessarily be more expensive than the solid hydrogen peroxide adducts mentioned herein. Another potential downside is that release of oxygen results in the production of aromatic compounds that may be absorbed systemically and produce toxic effects. In some embodiments the production of aromatic compounds is mitigated by incorporating the endoperoxides onto a non-bioavailable polymer.

In some embodiments, endoperoxides are used to deliver oxygen in any of the formulations for any of the therapeutic uses of EAT described herein.

Amount and Timing of Oxygen Administration

In some embodiments that EAT provides oxygen at a target site, for example the intestine or at least a portion thereof. In some embodiments, at least 3% oxygen (gas phase) is achieved for 24 hours or more. At least 3-5%, 5-10%, 10-25% oxygen is achieved for at least 12, 18, 24 or 48 hours in several embodiments. In one embodiment, oxygen concentration is increased by 20% or more (as compared to pretreatment levels) for at least 12 hours. In another embodiment, oxygen concentration is increased by 50% or more (as compared to pretreatment levels) for at least 6 hours. Prophylactically, 1-5% oxygen (gas phase) is achieved for several days, weeks, months or longer. In some embodiments, the desired oxygen level is achieved by repeated or continuous administration of the EAT compounds or agents disclosed herein, for example by administration 1, 2, 3, 4 or more times daily (in single or multiple doses or serving sizes per administration), and/or for a period of 1, 2, 3, 4, 5, 6, 7, or more days or weeks. In one embodiment, the API and/or catalyst are generally provided in doses of 250-1500 mg each per dose, and multiple doses per day may be provided. In one embodiment, the API and/or catalyst are provided in amounts to substantially achieve one or more of the following: at least 3% oxygen for 12 hours or more in a portion of the GI tract, reduce toxicity of undesired (e.g., anaerobic) microorganisms, reduce growth of undesired (e.g., anaerobic) microorganisms, and/or convert an anaerobic environment to an aerobic environment in at least a portion of the GI tract.

In several embodiments, a formulation is provided in which a catalase or other agent identified herein is encapsulated or otherwise contained within a material (such as a membrane, coating or other material). Such material, in one embodiment, (i) permits the diffusion of water, electrolyte, certain solutes and/or oxygen across the material, (ii) prevents all, substantially all or a majority (e.g., at least 50, 60, 70, 80, 90, 95%) of catalase (or other agent) from diffusing out of the material and (iii) prevents all, substantially all or a majority (e.g., at least 50, 60, 70, 80, 90, 95%) of digestive enzymes from diffusing into the material. In some embodiments, the agent comprises or consists essentially of oxygen carrier molecules and/or oxygen containing mixtures. In one embodiment, the material comprises pores that control diffusion. The catalyst, the API or both may be encapsulated, coated or otherwise formulated within means of controlling or regulating diffusion. In several embodiments, the oxygen producing agent as provided for herein (for example, granules contained within a capsule) is coated with one or more of an enteric coating, an osmotic coating, and a barrier coating. For example, in several embodiments, an agent as provided for herein is coated with two or more of an enteric coating, an osmotic coating, and a barrier coating.

EXAMPLES

The following are non-limiting examples according to several embodiments herein and other variants within the scope of the art also contemplated. In any of the examples below, an aerobic environment may be maintained for 6, 12, 18 or 24 hours, or longer according to some embodiments.

Example 1—Oxygen Carriers

A patient suffering from an anaerobic bacterial infection (e.g., of the GI tract such as the intestine) is identified. Infection may be diagnosed by, for example, symptoms, signs, clinical circumstances, biochemical clinical assay, and/or identification of the pathogen. Optionally, an amount, growth rate, and/or level of toxicity of the anaerobic bacteria is determined. The patient is administered a composition comprising at least one compound/agent that is an oxygen carrier molecule, for example an oxygen binding biomolecule (e.g., hemoglobin and/or myoglobin) and/or an oxygen containing mixture (e.g. an oxygen cocktail, microemulsions of oxygen gas bubbles, microemulsions of oxygen gas foams, or perfluorocarbons (e.g., perfluorocarbon oxygen solutions). One or more perfluorocarbons are used in several embodiments. Optionally the oxygen carrier molecule can be administered in combination with an oxygen prodrug or oxygen generating compound. The compound/agent is administered in an amount that is capable of creating an aerobic environment in target site (e.g., the lumen of the intestine) of the patient that inhibits the amount, growth rate and/or toxicity of the anaerobic bacterial infection, resulting in an improvement in the patient's condition. Optionally, after administration of the composition, the amount, growth rate and/or the level of toxicity of the anaerobic bacteria is determined. The administration of the composition can be repeated until the amount or growth of the anaerobic bacteria and/or the level of toxicity decreases to below a predetermined threshold and/or undesired symptoms subside.

Example 2—Oxygen Prodrugs

A patient suffering from an anaerobic bacterial infection (e.g., of the GI tract such as the intestine) is identified. Infection may be diagnosed by, for example, symptoms, signs, clinical circumstances (such as biochemical clinical assays), and/or identification of the pathogen. Optionally, an amount, growth rate, and/or level of toxicity of the anaerobic bacteria is determined. The patient is administered a composition comprising at least one compound/agent that is an oxygen prodrug or oxygen generating agent (e.g., an oxygen generating metal-peroxide salt or a hydrogen peroxide complex such as carbamide peroxide, calcium peroxide, calcium hydroxide, magnesium peroxide, sodium percarbonate, or an endoperoxide). Optionally the oxygen prodrug or oxygen generating agent can be administered in combination with an oxygen carrier molecule. The agent is administered in an amount that is capable of creating an aerobic environment in the target site (e.g., lumen of the intestine) of the patient that inhibits the amount, growth rate and/or toxicity of the anaerobic bacterial infection, resulting in an improvement in the patient's condition. Optionally, after administration of the composition, the amount, growth rate and/or the level of toxicity of the anaerobic bacteria is determined. The administration of the composition can be repeated until the amount or growth of the anaerobic bacteria and/or the level of toxicity decreases to below a predetermined threshold and/or undesired symptoms subside.

Example 3—*Clostridioides difficile* Infections & Oxygen Carriers

A patient suffering from a *Clostridioides difficile* infection of (e.g., of the GI tract such as the intestine) is identified. Infection may be diagnosed by, for example, symptoms, signs, clinical circumstances (such as biochemical clinical assays), and/or identification of the pathogen. Optionally, an amount, growth rate, and/or level of toxicity of the anaerobic bacteria is determined. The patient is administered a composition comprising at least one compound/agent that is an oxygen carrier molecule, for example an oxygen binding biomolecule (e.g., hemoglobin and/or myoglobin) and/or an oxygen containing mixture (e.g. an oxygen cocktail, microemulsions of oxygen gas bubbles, microemulsions of oxygen gas foams, or perfluorocarbons). Optionally the oxygen carrier molecule can be administered in combination with an oxygen prodrug or oxygen generating compound. The agent (e.g., compound) is administered in an amount that is capable of creating an aerobic environment in the target site (e.g., lumen of the intestine) of the patient that inhibits the amount, growth rate and/or toxicity of the *Clostridioides difficile*, resulting in an improvement in the patient's condition. Optionally, after administration of the composition, the amount, growth rate and/or the level of toxicity of the *Clostridioides difficile* bacteria is determined. The administration of the composition can be repeated until the amount or growth of the *Clostridioides difficile* bacteria and/or the level of toxicity decreases to below a predetermined threshold and/or undesired symptoms subside.

Example 4—*Clostridioides difficile* Infections and Oxygen Prodrugs

A patient suffering from a *Clostridioides difficile* infection (e.g., of the GI tract such as the intestine) is identified. Infection may be diagnosed by, for example, symptoms, signs, clinical circumstances (such as biochemical clinical assays), and/or identification of the pathogen. Optionally, an amount, growth rate, and/or level of toxicity of the anaerobic bacteria is determined. The patient is administered a composition comprising at least one agent that is an oxygen prodrug or oxygen generating agent (e.g., an oxygen generating metal-peroxide salt or a hydrogen peroxide complex such as carbamide peroxide, calcium peroxide, calcium hydroxide, magnesium peroxide, sodium percarbonate, or an endoperoxide). Optionally the oxygen prodrug or oxygen generating agent can be administered in combination with an oxygen carrier molecule. The agent is administered in an amount that is capable of creating an aerobic environment in the target site (e.g., lumen of the intestine) of the patient that inhibits the amount, growth rate and/or toxicity of the *Clostridioides difficile*, resulting in an improvement in the patient's condition. Optionally, after administration of the composition, the amount, growth rate and/or the level of toxicity of the *Clostridioides difficile* bacteria is determined. The administration of the composition can be repeated until the amount or growth of the *Clostridioides difficile* bacteria and/or the level of toxicity decreases to below a predetermined threshold and/or undesired symptoms subside.

Example 5—Food Poisoning and Oxygen Carriers

A patient suffering from food poisoning due to a foodborne infection (e.g., of the GI tract such as the intestine) caused by an anaerobic bacteria (e.g., *Clostridium perfringens*, botulism caused by *Clostridium botulinum*, *Clostridium butyricum*, and *Clostridium baratii*, cholera caused by *Vibrio cholera*, diarrheagenic *Escherichia coli* infection, and *Salmonella enteritidis*) is identified. Infection may be diagnosed by, for example, symptoms, signs, clinical circumstances (such as biochemical clinical assays), and/or identification of the pathogen. Optionally, an amount, growth rate, and/or level of toxicity of the anaerobic bacteria is determined. The patient is administered a composition comprising at least one agent that is an oxygen carrier molecule, for example an oxygen binding biomolecule (e.g., hemoglobin and/or myoglobin) and/or an oxygen containing mixture (e.g. an oxygen cocktail, microemulsions of oxygen gas bubbles, microemulsions of oxygen gas foams, or perfluorocarbons). Optionally the oxygen carrier molecule can be administered in combination with an oxygen prodrug or oxygen generating compound. The agent is administered in an amount that is capable of creating an aerobic environment in the target site (e.g., lumen of the intestine) of the patient that inhibits the amount, growth rate and/or toxicity of the foodborne infection of anaerobic bacterial, resulting in an improvement in the patient's condition. Optionally, after administration of the composition, the amount, growth rate and/or the level of toxicity of the foodborne anaerobic bacteria is determined. The administration of the composition can be repeated until the amount or growth of the foodborne anaerobic bacteria and/or the level of toxicity decreases to below a predetermined threshold and/or undesired symptoms subside.

Example 6—Food Poisoning and Oxygen Prodrugs

A patient suffering from food poisoning due to a foodborne infection (e.g., of the GI tract such as the intestine)

caused by an anaerobic bacteria (e.g., *Clostridium perfringens*, botulism caused by *Clostridium botulinum*, *Clostridium butyricum*, and *Clostridium baratii*, cholera caused by *Vibrio cholera*, diarrheagenic *Escherichia coli* infection, and *Salmonella enteritidis*) is identified. Infection may be diagnosed by, for example, symptoms, signs, clinical circumstances (such as biochemical clinical assays), and/or identification of the pathogen. Optionally, an amount, growth rate, and/or level of toxicity of the anaerobic bacteria is determined. The patient is administered a composition comprising at least one agent that is an oxygen carrier molecule, for example an oxygen binding biomolecule (e.g., hemoglobin and/or myoglobin) and/or an oxygen containing mixture (e.g. an oxygen cocktail, microemulsions of oxygen gas bubbles, microemulsions of oxygen gas foams, or perfluorocarbons). Optionally the oxygen carrier molecule can be administered in combination with an oxygen prodrug or oxygen generating compound. The agent is administered in an amount that is capable of creating an aerobic environment in the target site (e.g., lumen of the intestine) of the patient that inhibits the amount, growth rate and/or toxicity of the foodborne infection of anaerobic bacterial, resulting in an improvement in the patient's condition. Optionally, after administration of the composition, the amount, growth rate and/or the level of toxicity of the foodborne anaerobic bacteria is determined. The administration of the composition can be repeated until the amount or growth of the foodborne anaerobic bacteria and/or the level of toxicity decreases to below a predetermined threshold and/or undesired symptoms subside.

Example 7—Inflammatory Bowel Disease (IBD) and Oxygen Carriers

A patient suffering from IBD is identified e.g., diagnosed by those knowledgeable in the field. The patient is administered a composition comprising at least one agent that is an oxygen carrier molecule, for example an oxygen binding biomolecule (e.g., hemoglobin and/or myoglobin) and/or an oxygen containing mixture (e.g. an oxygen cocktail, microemulsions of oxygen gas bubbles, microemulsions of oxygen gas foams, or perfluorocarbons). Optionally the oxygen carrier molecule can be administered in combination with an oxygen prodrug or oxygen generating compound. The agent is administered in an amount that is capable of creating an aerobic environment in the target site (e.g., lumen of the intestine) of the patient that alleviates inflammatory processes, resulting in an improvement in the patient's condition, such as resolution or improvement of IBD symptoms and signs, including flare ups. Daily administration may be used to prevent exacerbations.

Example 8—Inflammatory Bowel Disease (IBD) and Oxygen Prodrugs

A patient suffering from IBD is identified e.g., diagnosed by those knowledgeable in the field. An IBD patient may have an anaerobic bacterial infection (e.g., of the intestine) that exacerbates the condition. Optionally, an amount, growth rate, and/or level of toxicity of the anaerobic bacteria is determined. The patient is administered a composition comprising at least one agent that is an oxygen carrier molecule, for example an oxygen binding biomolecule (e.g., hemoglobin and/or myoglobin) and/or an oxygen containing mixture (e.g. an oxygen cocktail, microemulsions of oxygen gas bubbles, microemulsions of oxygen gas foams, or perfluorocarbons). Optionally the oxygen carrier molecule can be administered in combination with an oxygen prodrug or oxygen generating compound. The agent is administered in an amount that is capable of creating an aerobic environment in the target site (e.g., lumen of the intestine) of the patient that alleviates inflammatory processes, resulting in an improvement in the patient's condition, such as resolution or improvement of IBD symptoms and signs. Daily administration may be used to prevent exacerbations.

Example 9—Constant Catalyst Concentration Formulation

Figure 1B:
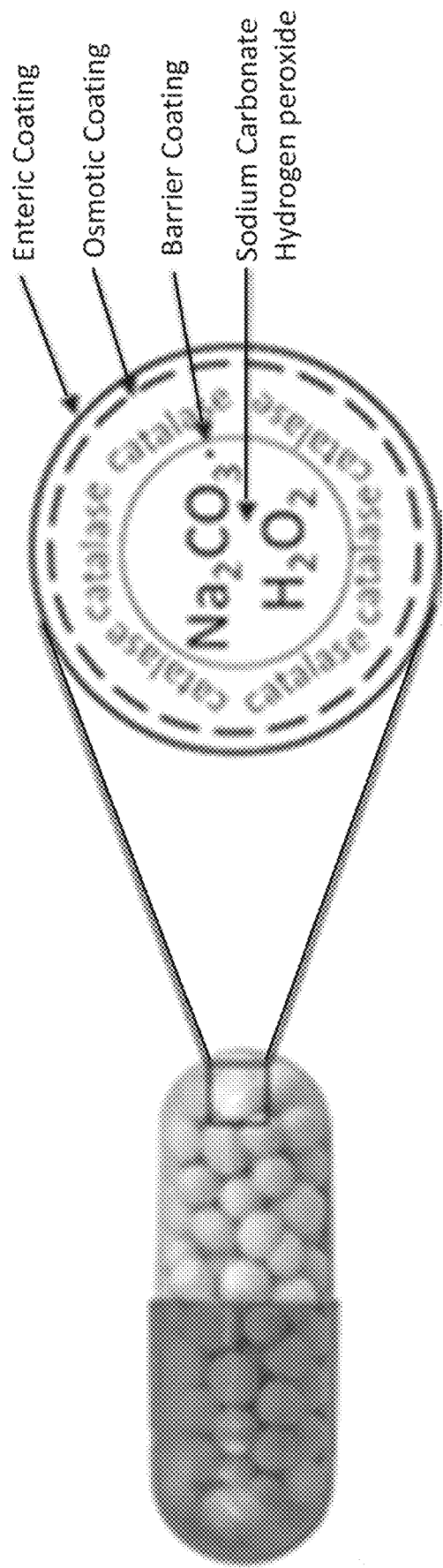
FIG. 1B is a graphical representation of another non-limiting embodiment of a formulation for delivery of oxygen via catalytic release of oxygen from an oxygen prodrug comprising multiple coatings.

FIG. 1A graphically represents an example formulation for delivery of oxygen via catalytic release of oxygen from an oxygen prodrug. In FIG. 1A the thick solid line represents an enteric coated osmotic membrane encasing the capsule or tablet's contents. The oxygen prodrug is represented by API which is encased in a controlled release coating (thin line around API). The controlled release coating further serves to extend shelf life by preventing the API from coming into contact with the catalase catalyst powder. The enteric coating prevents water from penetrating into the capsule or tablet until the capsule or tablet reaches the target site such as the intestine. FIG. 1B represents an additional embodiment of a formulation for delivery of oxygen via catalytic release of oxygen from an oxygen prodrug. In FIG. 1B, the formulation is shaped into granules for delivery in a capsule, for example, and the outer solid line represents an enteric coating surrounding the contents of each individual granule (only one granule is shown in the schematic, for clarity). The oxygen prodrug, sodium carbonate hydrogen peroxide as a non-limiting example, centrally located in the granule and is surrounded by a barrier coating. The barrier coating further serves to extend shelf life by preventing the oxygen prodrug from coming into contact with enzymatic catalyst, such as catalase. The enteric coating prevents water from penetrating into the capsule or tablet until the capsule or tablet reaches the target site such as the intestine. Positioned between the enteric coating and the catalyst is an osmotic coating (dashed line in FIG. 1B). The osmotic coating has a pore size is sufficiently large enough to allow water to pass through the coating following osmotic pressure and dissolving and activating the catalase catalyst. The catalase, in one embodiment, cannot diffuse across the osmotic coating because the pore size is too small, maintaining the catalase at a constant concentration (e.g., within an individual granule). The catalase is not degraded by digestive enzymes because the pore size is too small to allow digestive enzymes to diffuse inside the granule.

Figure 2:
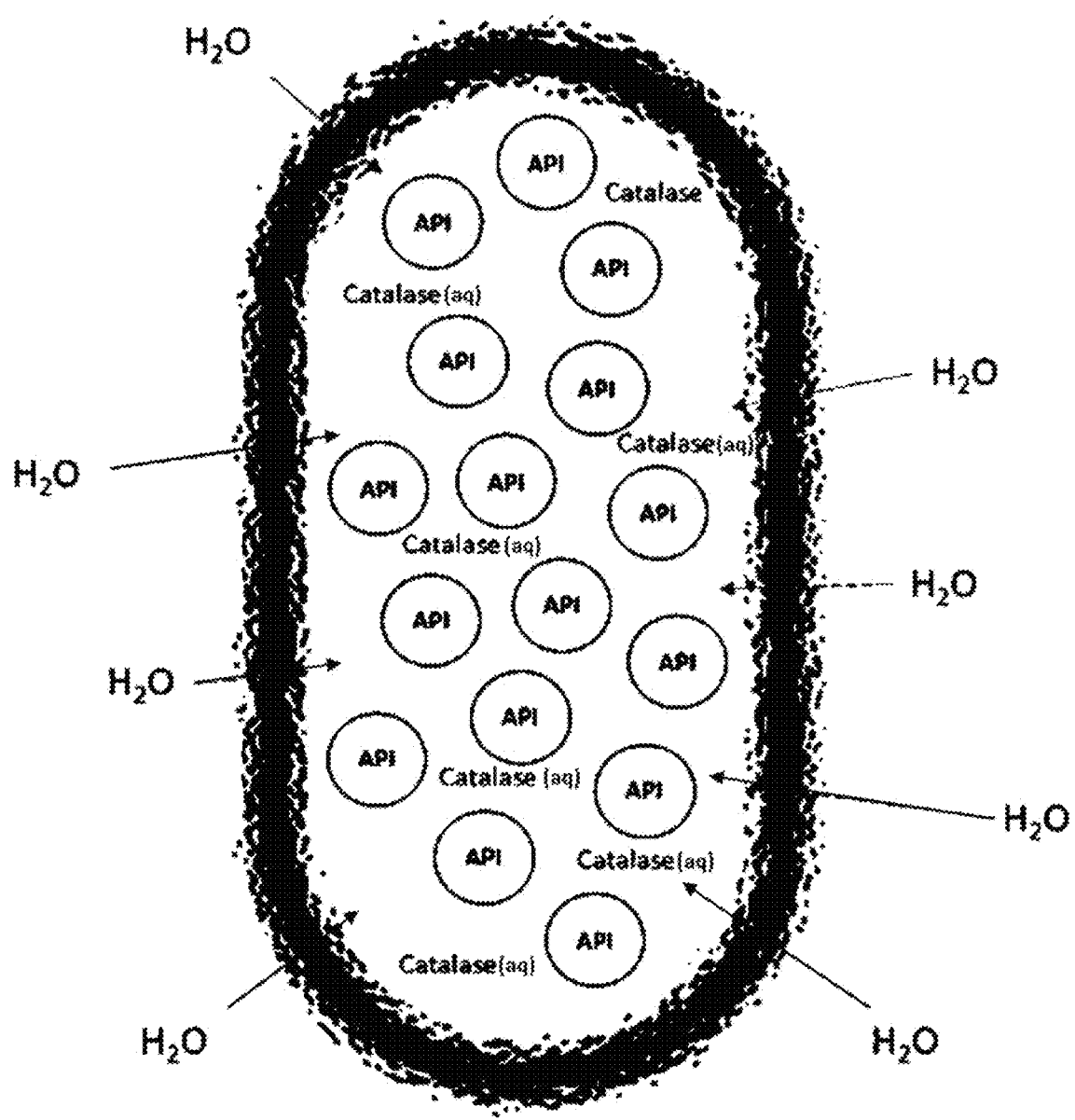
FIG. 2 is a graphical representation of the embodiment of FIG. 1A depicting the capsule or tablet in the target site (e.g., intestine) after the enteric coating has dissolved.

FIG. 2 depicts, in one embodiment, the capsule or tablet in the target site (e.g., intestine) after the enteric coating has dissolved leaving the exposed osmotic membrane represented by the fuzzy line encasing the capsule or tablet's contents. The osmotic membrane's pore size is sufficiently large enough to allow water to cross the membrane following osmotic pressure and dissolving and activating the catalase catalyst. The catalase, in one embodiment, cannot diffuse across the osmotic membrane because the pore size is too small, maintaining the catalase at a constant concentration (e.g., within the capsule, caplet, tablet and the like). The catalase is not degraded by digestive enzymes because the pore size is too small to allow digestive enzymes to diffuse inside the capsule or tablet. In FIG. 2, the controlled release coating has not yet begun to dissolve as represented by the intact line surrounding the API.

Figure 3A:
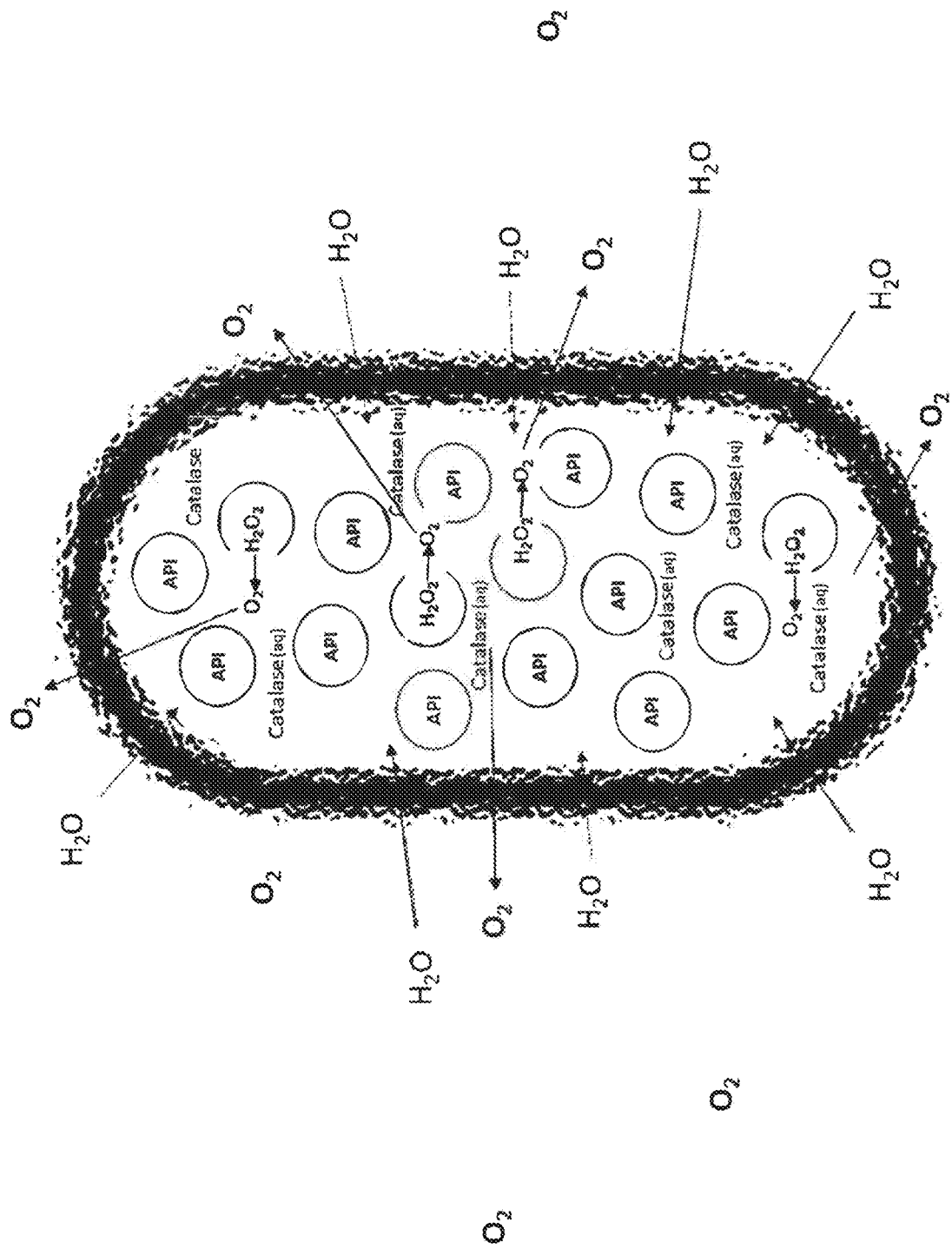
FIG. 3A is a graphical representation of the embodiment of FIG. 1A, depicting the capsule or tablet as the controlled release coating begins to dissolve releasing hydrogen peroxide which is efficiently converted to oxygen and water.
Figure 3B:
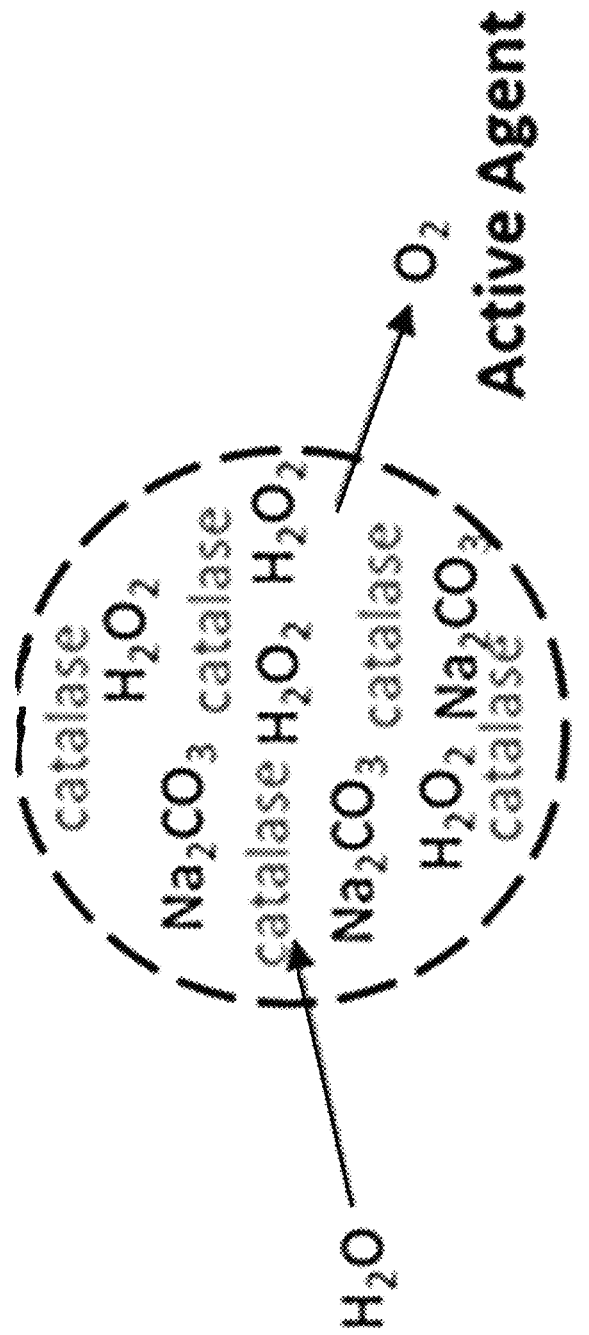
FIG. 3B is a graphical representation of the non-limiting embodiment of FIG. 1B, depicting individually coated granules as the controlled release coating begins to dissolve releasing hydrogen peroxide which is efficiently converted to oxygen and water.

FIG. 3A shows, in one embodiment, the capsule or tablet as the controlled release coating begins to dissolve releasing hydrogen peroxide which is efficiently converted to oxygen and water according to Equation 1 by the catalase enzyme. The oxygen thus produced diffuses across the osmotic membrane, aerobicizing the intestinal lumen. In several embodiments, other tissue sites may be treated. Likewise, FIG. 3B shows a schematic of an individual granule (or tablet or the like) as the enteric coating has been dissolved (for example, for example, after reaching a target site, like the intestine) and allows for water to cross the osmotic coating and activate the catalase, which acts on the sodium carbonate hydrogen peroxide (or other oxygen prodrug) to release hydrogen peroxide which is efficiently converted to oxygen and water according to Equation 1.

Figure 14:
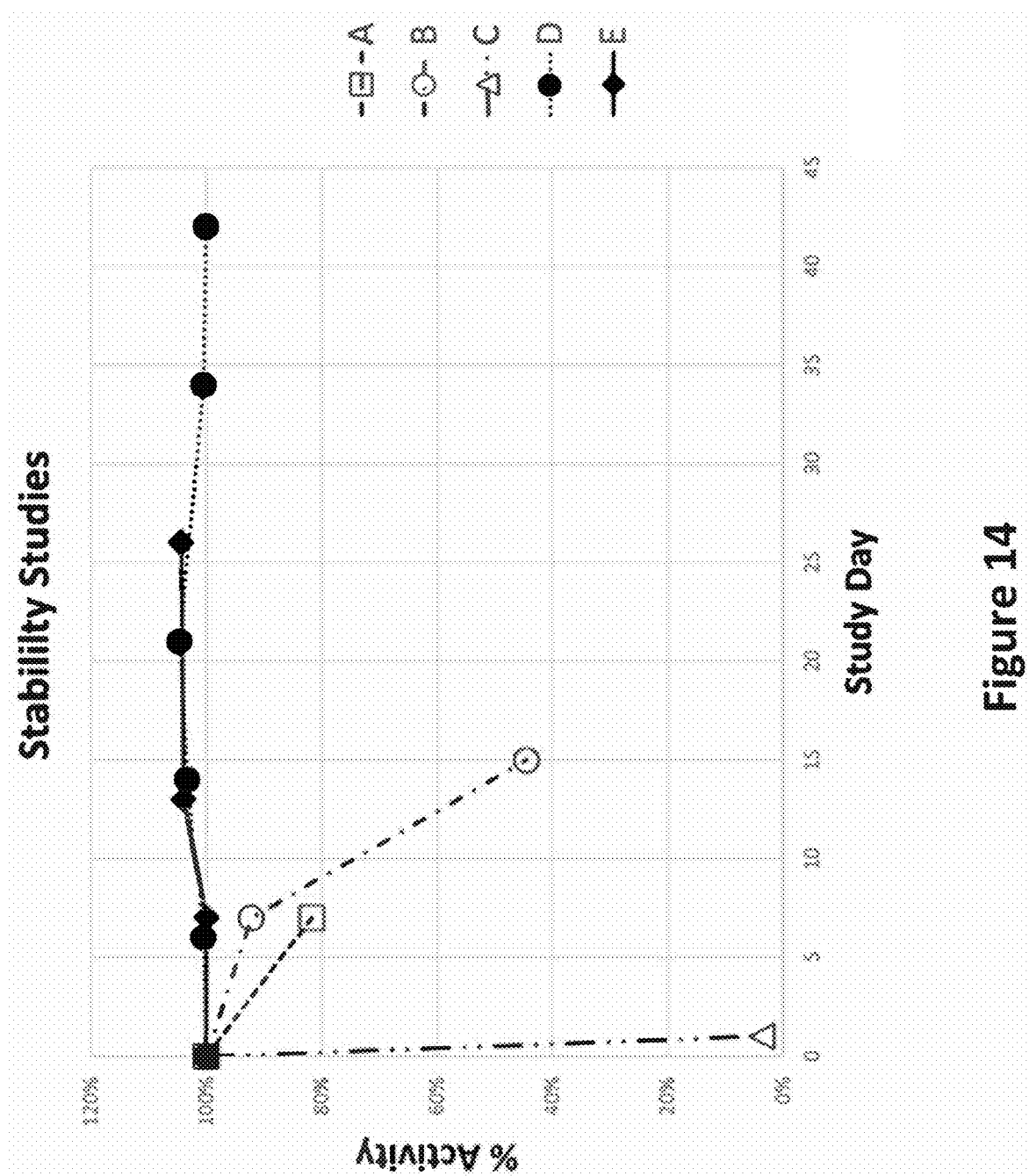
FIG. 14 depicts the results of stability testing of various formulations according to embodiments herein and stored according to various conditions.

Example 10—Stability Testing of Different Methods of Composing and Storing Catalyst and Oxygen Prodrug This experiment was designed to evaluate various formulations of the prodrug and catalyst, various storage conditions and structures of the drug delivery device and their impact on the extended oxygen producing capability prodrug. The results of this experiment are illustrated in FIG. 14. Several embodiments provided for herein advantageously allow for stable oxygen delivery. Further advantages are associated with some embodiments, including but not limited to, relatively high access to ingredients, reduced costs of manufacturing, and enhanced stability, even at room temperature.

A 10:10:80 mixture containing 1000 Baker units/gram catalase:instant setting starch:sodium percarbonate by mass was prepared. The mixture was made by adding the individual components into a large glass vial followed by vortex mixing. Immediately after mixing, an aliquot containing 240 mg of sodium percarbonate was assayed for oxygen producing activity. This initial assay (i.e., Time 0) produced 21.3 cc of gaseous oxygen which was defined as 100%. After 7 days of storage at room temperature, the assay was repeated. The second assay produced 17.4 cc of gaseous oxygen or 82% of the original volume. This mixture lost 18% of its oxygen producing capacity after 7 days at room temperature. This data is shown as Plot A (open squares) of FIG. 14.

A mixture of 10% 1000 Baker units/gram catalase and 90% sodium percarbonate by mass was prepared by mixing the ingredients by mechanical vortexing and stored at room temperature. Volumetric assay immediately after mixing with an aliquot containing 260 mg of sodium percarbonate yielded 27.0 cc of gaseous oxygen which was defined as 100% (Time 0). Assays repeated at 7 and 15 days after mixing revealed a loss of 8% and 56%, respectively, see Plot B (open circles).

A 50:50 by mass mixture of baker's yeast and sodium percarbonate was mixed with a mortar and pestle, then stored in a glass vial at room temperature. Immediately after mixing (Time 0), an aliquot containing 260 mg of sodium percarbonate was assayed for oxygen producing activity and yielded 27.0 cc of oxygen which was defined as 100%. During the day, water condensate was observed on the sides of the storage glass vial consistent with the disproportionation of hydrogen peroxide to water and oxygen. One day after mixing, only 1 cc (or 4% of the original volume) representing a loss of 96% oxygen producing capacity was observed (Plot C, open triangles). This confirms the loss the hydrogen peroxide oxygen prodrug due, at least in part to the contact between the prodrug and the catalyst during storage, and/or the temperature of storage.

A mixture of 10% 1000 Baker units/gram catalase and 90% sodium percarbonate were mixed by mechanical vortexing and stored refrigerated at 4° C. Volumetric assay immediately after mixing (Time 0) with an aliquot containing 240 mg of sodium percarbonate yielded 21.3 cc of gaseous oxygen which was defined as 100%. Multiple subsequent assays repeated through day 42 post-mixing demonstrated no loss of oxygen producing capacity (Plot D, closed circles). These data demonstrate that, even when contacting the catalyst, the prodrug can remain stable, if refrigerated (contrast with Plot B). In several embodiments, oral formulations provided for herein are optionally stored below room temperature (e.g., approximately 4° C.), along with the resultant enhanced stability/oxygen capacity maintenance. In several embodiments, oral formulations provided for herein are optionally stored frozen (e.g., approximately −20° C.), with the further enhanced stability/oxygen capacity maintenance.

An additional experiment was undertaken to evaluate the further enhancement in stability and long-term oxygen generation potential of formulations according to embodiments disclosed herein in which the catalyst and prodrug are separated from one another until they reach a desired site of action (such as the small or large intestine). A structure designed to mimic the capsule-in-a-capsule structure disclosed herein (or coated prodrug within coated catalyst). Size 1 gelatin capsules were filled with sodium percarbonate and buried in 100 grams of Baker's yeast. This simulates a capsule-in-a-capsule structure where the outer capsule contains baker's yeast surrounding the inner capsule and stored at room temperature (22° C.). With this arrangement, the outer surface area of the inner capsule is completely surrounded by the yeast, as it would be if the yeast/catalyst were also in a capsule/coated. On day 0, 255 mg of the sodium percarbonate from an inner capsule yielded 25.3 cc of gaseous oxygen which was defined as 100%. Repeated testing showed no loss of activity through 26th day post-mixing. This data demonstrates that, according to certain embodiments discussed herein, a mixture of the prodrug (e.g., sodium percarbonate) is stable at room temperature for at least 20 days when the prodrug and catalyst (e.g., catalase) are compressed and stored in a capsule-in-a-capsule device at room temperature. In addition, this data demonstrates that biological sources of catalase, such as yeast, can be used to convert the prodrug to oxygen and water. Advantageously, yeast (or other microorganism or biological sources of catalase) are renewable-yeast replicates naturally, so cost of goods can be substantially reduced. Additionally, the stabilizing effect of yeast on the formulation led to unexpectedly robust preservation of oxygen-generating capacity, even at room temperature storage. This indicates that such formulations may be more effective in oxygenation of an intestinal region of a subject living in an environment where refrigeration may not be readily available, thereby expanding the potential geographies in which oxygenation therapy can successfully be administered (and at lower cost).

Example 11—Animal Model Efficacy of Enteric Aerobization

There are two models of *Clostridioides difficile* infection that are commonly used in the evaluation of new treatments. Hamsters succumb to CDIs with severe infections resulting in high mortality. Some experts prefer the mouse model because it is more humanlike in behavior. Mouse CDI is less severe with lower mortality rates and have recurrent infections in the antibiotic control group similar to humans.

Because of the more humanlike characteristics for mouse CDI model, it was chosen to evaluate enteric aerobization.

Administration of enteric aerobization therapies presented several challenges with the mouse model. Administration of experimental compounds in rodents is normally performed via gastric gavage using a solution of the test article. however, this could not be accomplished with enteric aerobization therapy because dissolving the mixture prior to administration would result in premature loss of oxygen effervescence before entering the intestine. Further, there is uncertainty that rodents reliably pass enteric coated capsules or tablets from the stomach to the intestine. And the pH gradient in rodents is shallower than in humans suggesting that enteric coating may not work reliably. Finally, the small capsule or tablet sizes required for rodent administration severely limits dosages. Duodenal cannulated mice were used for the direct aerobization of the models' intestinal track via direct infusion of oxygen.

Thirty C57BL/6 female mice (18-22 g) fitted with duodenal catheters externalized and fitted with access button ports were purchased from Charles River Laboratories and singly housed in a temperature and humidity-controlled room with a 12-hour light cycle. The mice were divided into 3 groups of 10. All procedures used in these experimental protocols were in compliance with the Animal Welfare Act, the Guide for the Care and Use of Laboratory Animals, and the Office of Laboratory Animal Welfare.

The mice were pretreated with an antibiotic cocktail in their drinking water for 8 consecutive days. This antibiotic cocktail was composed of 1% glucose, 500 mcg/mL kanamycin, 44 mcg/mL gentamicin, 1062.5 units per milliliter colistin, 269 mcg/mL metronidazole, 156 mcg/mL ciprofloxacin, 100 mcg/mL ampicillin, and 56 mcg/mL vancomycin. The antibiotic cocktail and drinking water were replaced every 2 to 3 days. Five days prior to infection the antibiotic water was removed and normal drinking water was provided to the animals. Three days prior to infection the animals received a single dose of clindamycin 10 mg per kilogram via oral administration in a volume of 10 mL per kilogram. Other antibiotics and antimicrobials may be used according to several embodiments of the invention. Other tissues sites in the GI tract or elsewhere may be treated.

On study Day 0 mice were inoculated with the bacterial suspension of $5 \times 10^5$ CFU *Clostridioides difficile* ATCC 43255 via oral gavage. Eight hours after inoculation administration of vehicle, antibiotic control, and test article was initiated according to the following. The vehicle a.k.a. infection control group of 10 mice received 80 μL per hour 100% pure nitrogen gas via duodenal catheter. The infection control group of 10 mice received 50 mg/kg vancomycin via oral gavage once daily. The experimental group of 10 mice received 80 μL per hour 100% oxygen test article via duodenal catheter. Administration was continued from study day 0 to study day 4, a total of 5 days. The mice were followed for 14 days after inoculum recording daily weights and clinical observations. Animals that appeared severely moribund were euthanized. At the end of the study all animals were humanely euthanized.

The experimental protocol, according to one embodiment, is depicted in FIG. 4.

Survival Results

Figure 5:
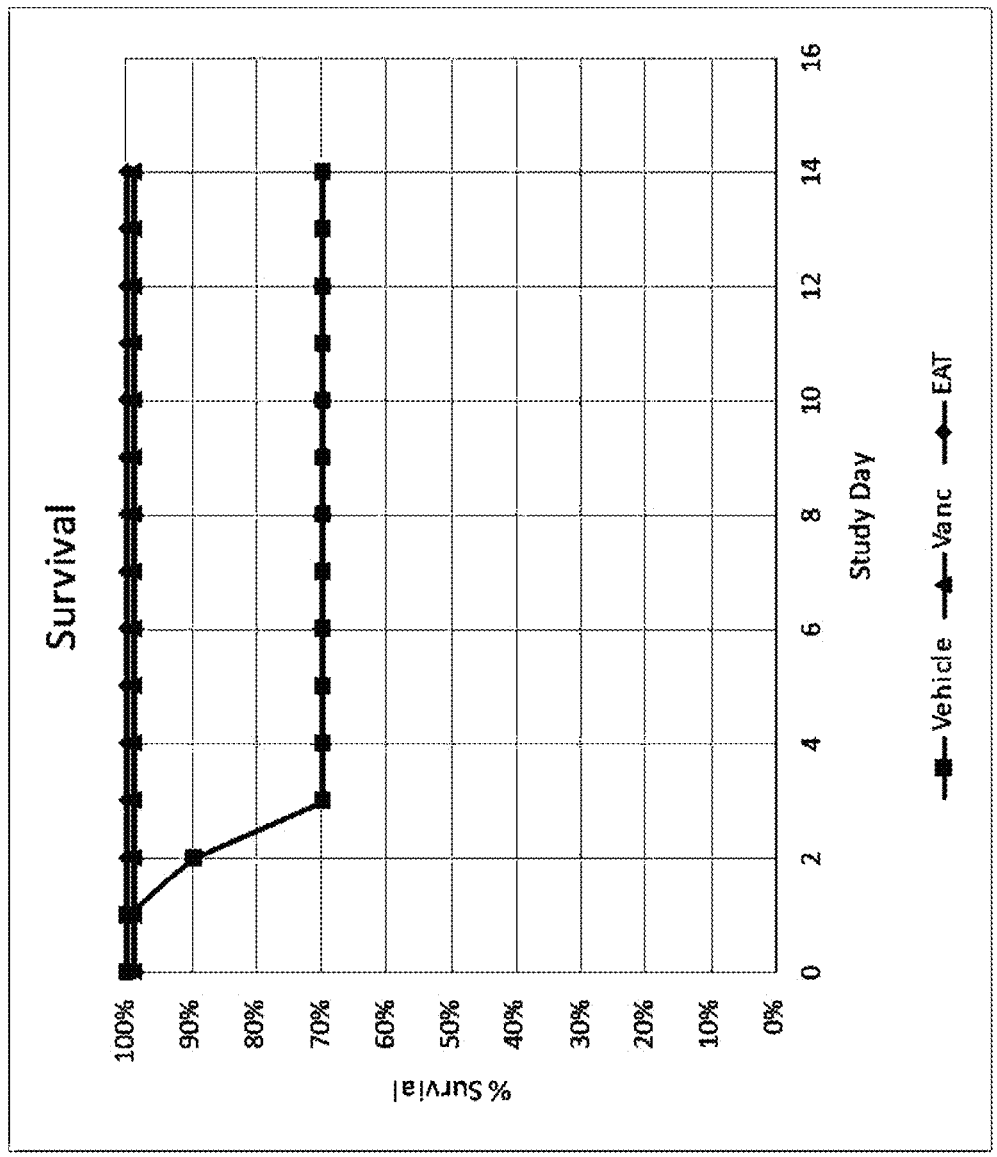
FIG. 5 depicts the results of the experimental protocol depicted in FIG. 4 showing the percent survival of three treatment groups: control treatment (vehicle), the antibiotic vancomycin (Vanc), and enteric aerobization therapy (EAT).

The infection (a.k.a. vehicle, placebo, nitrogen) control group suffered a 30% mortality (70% survival). Both the EAT (a.k.a. oxygen, test, experimental) group and the antibiotic (a.k.a. vancomycin) control group conferred 100% survival (no mortality). These results are displayed in FIG. 5.

Clinical Cure Results

Figure 7:
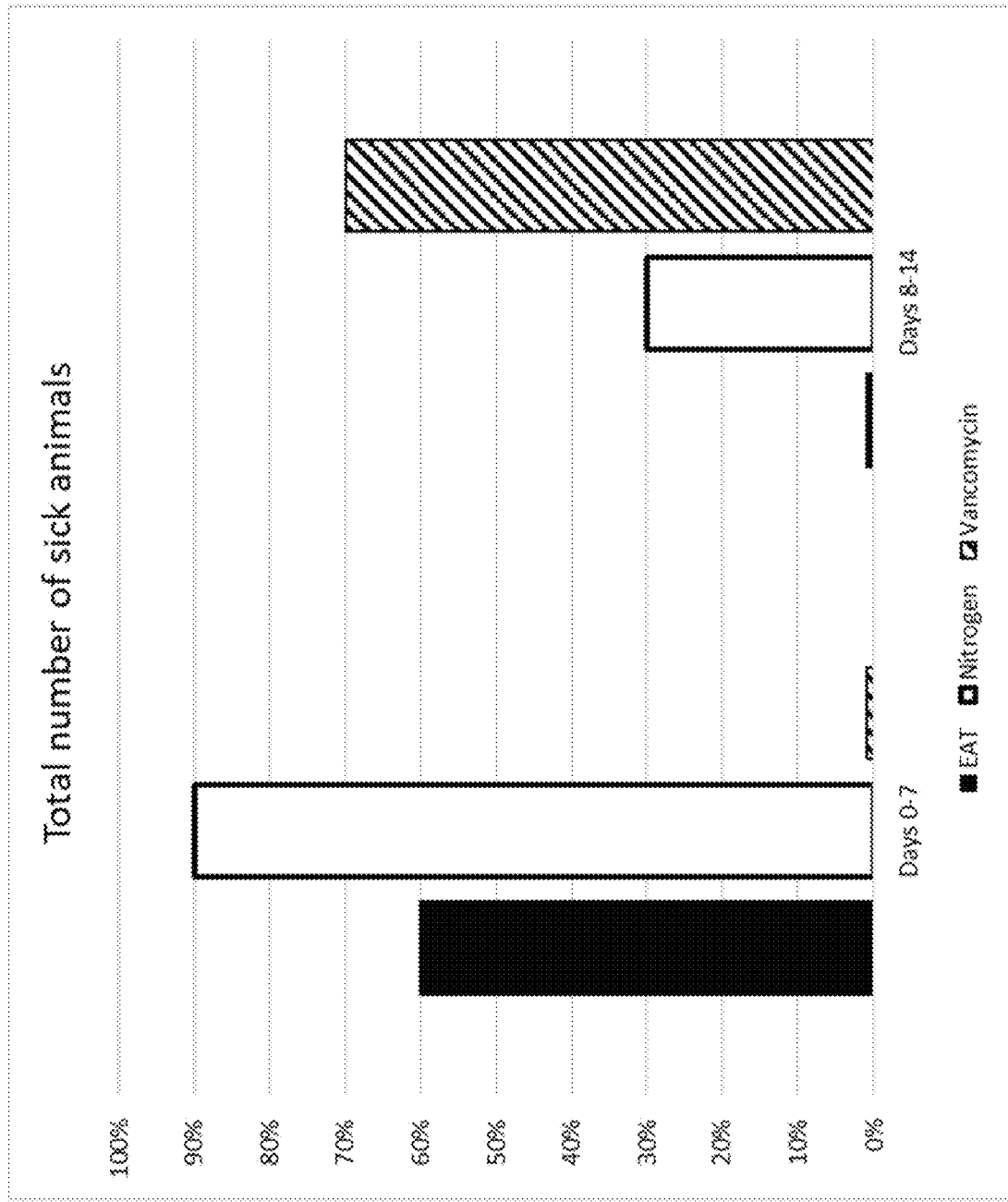
FIG. 7 depicts the results of the experimental protocol depicted in FIG. 4, showing the number of animals in each group (EAT, vehicle (nitrogen), vancomycin) that displayed at least one clinical observation according to the observation scale depicted in FIG. 6 during the 1st week after inoculation (days 0-7) and the 2nd week after inoculation (days 8-14).

Reflecting the group's mortality only 70% of the infection control group recovered from the CDI. FIG. 7 shows the number of animals in each group that displayed at least one clinical observation according to the table in FIG. 6 divided into the 1st week after inoculation and the 2nd week after inoculation. These results can also be seen in FIG. 8 which displays the number of animals with at least one clinical finding on a daily basis.

Figure 8:
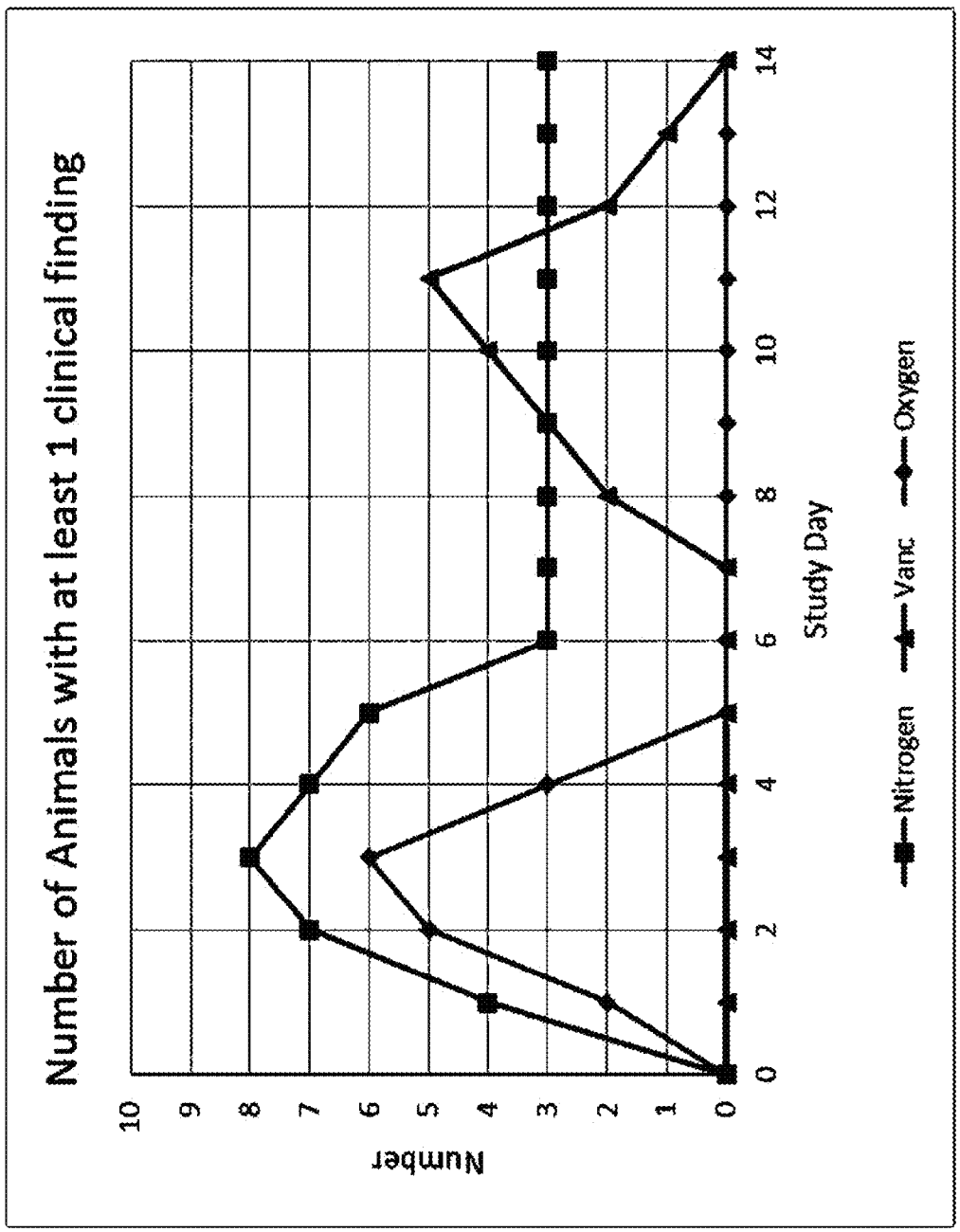
FIG. 8 depicts the results of the experimental protocol depicted in FIG. 4 showing the number of animals with at least one clinical finding on a daily basis for each of the three treatment groups: control (nitrogen), vancomycin (Vanc), and EAT (oxygen).

Also seen in FIGS. 7 and 8 is the apparent rapid onset of vancomycin in the antibiotic control group. However, this potent early efficacy did not translate into a high clinical cure. Seventy percent of the animals in the antibiotic control group showed signs of infection in the 2nd week after inoculation and treatment. Such recurrences are also seen in humans treated with antibiotics for CDI.

FIG. 7 shows that EAT had a protective effect with fewer sick animals compared to the infection control group, though not as protective early on as they antibiotic control group. As will be seen in the following section the sick animals in the EAT group were not as sick as those in the infection control group. In FIG. 8 it can be seen that the animals in the EAT group recover rapidly. Most importantly these figures show no recurrent infections in the EAT group, i.e., 100% cure rate.

Clinical Severity Results

Figure 9:
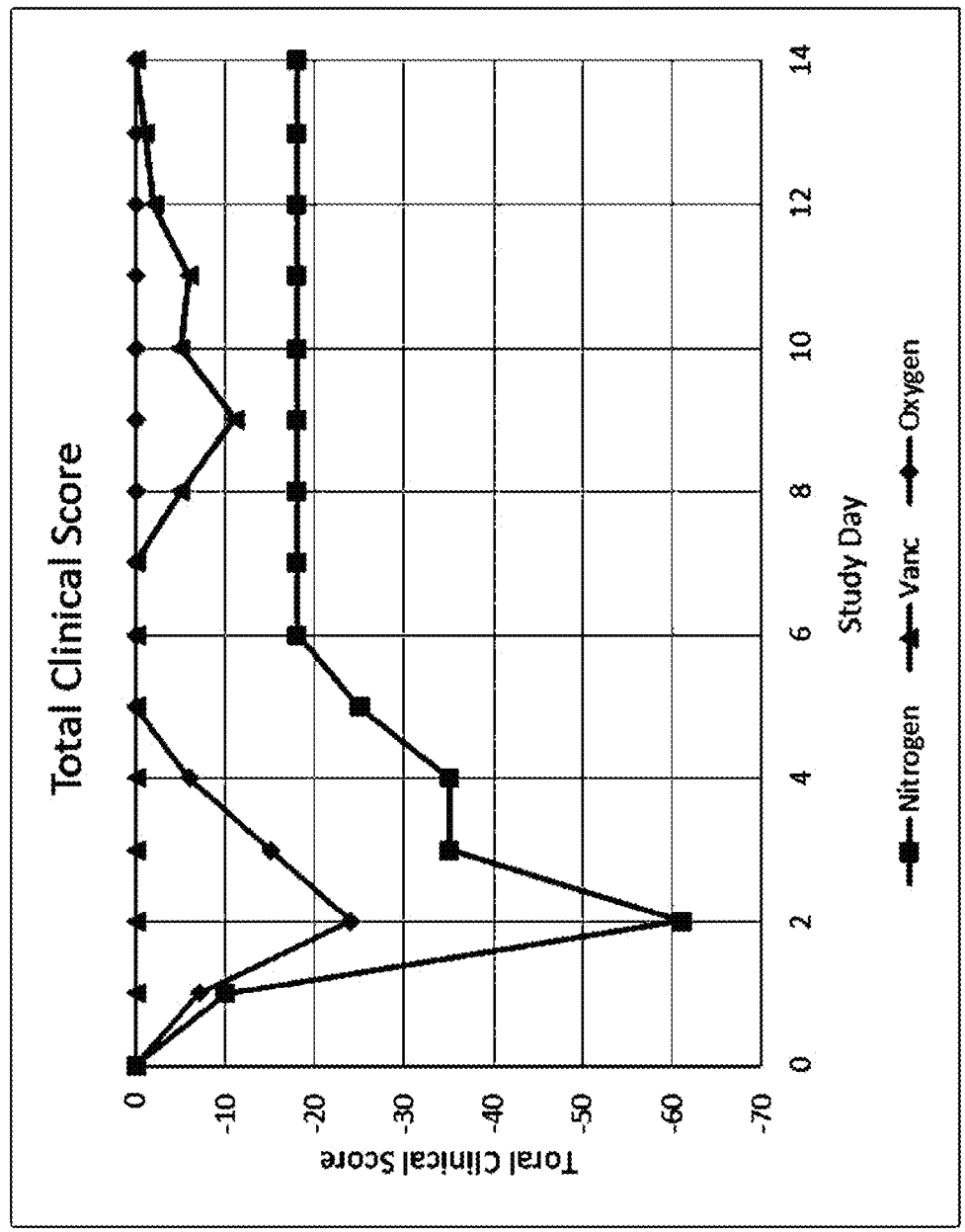
FIG. 9 depicts the results of the experimental protocol depicted in FIG. 4 showing the total clinical score for each of the three treatment groups: control (nitrogen), vancomycin (Vanc), and EAT (oxygen).
Figure 10:
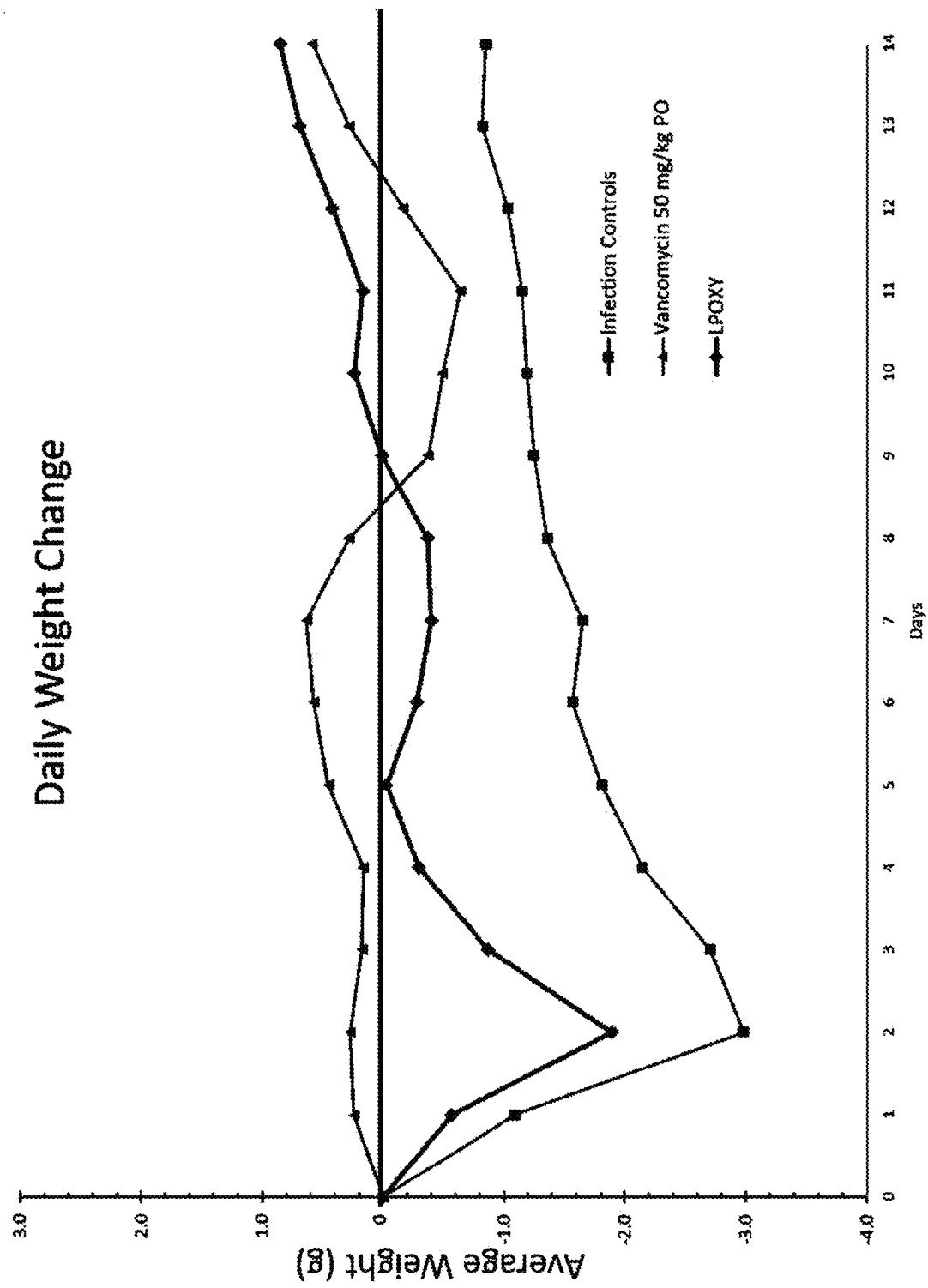
FIG. 10 depicts the results of the experimental protocol depicted in FIG. 4 showing the daily weight change record for each of the three treatment groups: control (nitrogen), vancomycin, and EAT (LPOXY).

The data in FIG. 9 confirm that the animals treated with EAT are mildly ill compared to the infection control group, recover rapidly, and have a 100% cure rate compared to the infection and antibiotic control groups. The daily weight change record displayed in FIG. 10 confirm these observations. The small dip in weights between days 5 and 9 in FIG. 10 do not represent recurrence since there are no clinical findings in the preceding plots. The slower onset of action of EAT seen in these experiments is to be expected because the oxidative conditions are hostile to *Clostridioides difficile*, the organism is able to withstand higher oxygen tensions for short amounts of time, 24 to 36 hours. While the organism is able to survive higher oxygen tensions however it does not thrive.

Tolerability

In a separate experiment using the above conditions the tolerance of bolus injection of 100% oxygen gas was tested. No adverse effects were observed up to the maximum bolus tested, 200 microliters every 6 hours (8 mL/kg per bolus; 32 mL/kg/day). In these efficacy experiments, no adverse effects due to nitrogen or oxygen gas infusions were observed (3.2 mL/kg/hr; 76.8 mL/kg/day). In fact, 1 animal in the nitrogen group and 3 animals in the oxygen group without symptoms were lively enough that they chewed through their infusion lines which had to be replaced.

Summary Results

These results demonstrate that aerobization of an animal intestine is well tolerated and produces a hostile environment for *Clostridium difficile*. Enteric aerobization therapy reduces the severity of disease, accelerates recovery, and produces a 100% cure rate in the mouse CDI model. The vancomycin antibiotic control has a more rapid onset of action, but only delivered a 30% cure rate with 70% of the animals showing clinical signs of recurrence after treatment was complete. According to other embodiments, a hostile environment for undesired organisms other than or in addition to *Clostridium difficile* will be created.

Example 12—Testing of Coated Granules

This experiment was designed to evaluate the stability and oxygen release of an oxygen generating formulation as provided for herein. This experiment tested the oxygen release rate of granules at various stages of production of granules comprising individual enteric, osmotic and barrier coatings (see, for example, FIG. 1B). The individually coated granules were generated using the non-limiting ingredients and amounts shown in Table 2.

TABLE 2

Multi-Coated Granule Specification

| Component | Purpose | Amount per gram | Amount per unit |
|---|---|---|---|
| Sodium Carbonate-Hydrogen Peroxide (2/3) | Precursor to the Active Ingredient | 568.6 mg | 284.3 mg |
| Klucel EF Pharm | Binder and Barrier Layer for Pellet Core | 63.1 mg | 31.55 mg |
| Catalase | Activator | 13.0 mg | 6.5 mg |
| Hydroxypropyl Methylcellulose E3 | Binder and Coating for Pellet Outer Layer | 3.2 mg | 1.6 mg |
| Eudragit NE 30D | Sustained Release Coating | 26.3 mg | 13.15 mg |
| Talc | Dispersent | 26.3 mg | 13.15 mg |
| Eudragit L30D-55 | Enteric Coating | 256.5 g | 128.25 mg |
| Plasacryl HTP20 | Glidant and Plasticizer | 43.5 mg | 21.75 mg |
| Hard Gelatin Capsule | Capsule Shell | N/A | 1 ea |

Test granules were generated by application of aqueous coatings applied via a fluid bed application. Granules were made with various coatings to compare the functionality of the coatings. A first group of granules was made with sodium percarbonate, a barrier coating, and catalase. A second group of granules was made with sodium percarbonate, a barrier coating, catalase, and an osmotic coating. A third group of granules was made with sodium percarbonate, a barrier coating, catalase, an osmotic coating, and an enteric coating. For the third group, the gross density of the granules was 0.95 g/cc. Individually, the granule density is >1.0 g/cc based on the observation during the experiment that they sank to the bottom of the aqueous solutions in which they were tested.

To simulate conditions of the stomach, 500 mg of the granules from Group 3 was placed in 50 mL of simulated gastric fluid (RICCA catalog #7108-16) with stirring in a volumeter (screw-cap bottle equipped via a rubber stopper and tubing to a glass syringe). No reaction was observed during the first 30 minutes. After 30 minutes, particles that previously sank, rose from the bottom of the test vessel and floated to the upper region of the solution, consistent with gas production. Very slow effervescence was observed as bubbles during the next hour (1.5 hours total), but insufficient gas was released to be detected by the volumeter (<1 mL).

To simulate conditions once administered oxygen producing formulations have passed through the stomach and reside in the intestine, an additional experiment was performed. For this experiment, granules from Groups 1 and 2 were tested in 100 mL of 100 mM pH 6.8 sodium phosphate buffer, while granules from Group 3 was tested in 50 mL of pH 7.0 simulated intestinal fluid (RICCA catalog #7109.75-16). Initially, granules in each group sank to the bottom of the test vessel. After about 20 minutes of stirring, effervescence began. Subsequently, granules floated to the test media an exhibited robust effervescence, which was measured in the volumeter. Effervescence was complete within 75 minutes from initiation of the experiment. While granules remained floating after complete effervescence, after being left overnight, the granules had again sunk to the bottom of the reaction vessel. Data is summarized in Table 3, below.

TABLE 3

| | | Oxygen Production | | | |
|---|---|---|---|---|---|
| Test Article | Test Mass | % Sodium percarbonate | Cc Oxygen Released | Theoretical Oxygen Yield | % Yield |
| Group 1 | 500 mg | 82 | 45 | 44 | 102 |
| Group 2 | 500 mg | 76 | 42 | 41 | 102 |
| Group 3 | 455 mg | 57 | 22 | 28 | 79 |

These data demonstrate that, according to certain embodiments disclosed herein, a granule (or other form of an oxygen generating composition) allow the production of significant quantities of oxygen. The addition of multiple coatings on an individual granule (e.g., enteric coating, osmotic coating, and a barrier coating) result in a reduced percentage of the granule corresponding to an active agent (or pre-active agent). Here, these data demonstrated that, even with only 57% of a given granule being made up of the pre-oxygen component (sodium percarbonate here as a non-limiting embodiment), the resulting oxygen production is nearly 80% of the theoretical yield. Additionally, the use of multiple coatings on an individual granule (e.g., enteric coating, osmotic coating, and a barrier coating) are believed to impart additional stability to the granule in the target environment (such as the intestine), which may lead to improved therapies by delivering oxygenation of the surrounding environment.

Although certain embodiments and examples have been described herein, aspects of the embodiments shown and described in the present disclosure may be differently combined and/or modified to form still further embodiments. The section headings used herein are merely provided to enhance readability and are not intended to limit the scope of the embodiments disclosed in a particular section to the features or elements disclosed in that section. Moreover, although features may be described above as acting in certain combinations, one or more features from a claimed combination can, in some cases, be excised from the combination, and the combination may be claimed as a subcombination or variation of a subcombination. For purposes of this disclosure, certain aspects, advantages, and novel features are described herein. Not necessarily all such advantages may be achieved in accordance with any particular embodiment. Thus, for example, the disclosure may be embodied or carried out in a manner that achieves one advantage or a group of advantages as taught herein without necessarily achieving other advantages as may be taught or suggested herein. Methods disclosed herein need not be performed in the order recited. The methods disclosed herein include certain actions taken by a practitioner; however, they can also include any third-party instruction of those actions, either expressly or by implication. Additionally, the methods described herein may be practiced using any agent suitable for performing the recited steps. Various embodiments of the disclosure have been presented in a range format. It should be understood that the description in range format is merely for convenience and brevity and should not be construed as an inflexible undue limitation on the scope of the invention. The ranges disclosed herein encompass any and all overlap, sub-ranges, and combinations thereof, as well as individual numerical values within that range. Language such as "up to," "at least," "greater than," "less than," "between," and the like includes the number recited. Numbers preceded by a term such as "about" or "approximately" include the recited numbers. For example, "approximately or about 30-50%" includes 30% and 50%. The terms "generally" and "substantially" as used herein represent an amount close to the stated amount that still performs a desired function or achieves a desired result.

What is claimed is:

1. An oral formulation in solid form for inhibiting intestinal anaerobic bacteria comprising a plurality of individually coated granules contained within a capsule, wherein each coated granule comprises:
    an oxygen prodrug,
        wherein the oxygen prodrug is encased within a controlled release coating;
    a catalyst,
    wherein the catalyst controls the rate of conversion of the oxygen prodrug to oxygen at a target site in an intestine of a subject,
        a semipermeable coating surrounding the catalyst and the oxygen prodrug, wherein the semipermeable coating has a pore size that prevents at least a majority of the catalyst from diffusing out of the semipermeable coating and prevents at least one intestinal digestive enzyme from diffusing into the semipermeable coating, and
        an enteric coating;
    wherein when orally administered to a subject and upon reaching the target site in the intestine of the subject, the catalyst catalyzes conversion of the oxygen prodrug to generate oxygen and create an aerobic environment at the target site in the intestine of the subject sufficient to inhibit growth or toxicity of a population of anaerobic bacteria in the intestine.

2. The oral formulation of claim 1,
    wherein the population of anaerobic bacteria comprises *Clostridioides difficile*,
    wherein the oxygen prodrug is selected from sodium percarbonate, hydrogen peroxides, endoperoxides, carbamide peroxide, calcium peroxide, magnesium peroxide, and combinations thereof, and
    wherein the catalyst is selected from catalase, iodide, manganese dioxide, iron (III), silver, dichromate, and combinations thereof.

3. The oral formulation of claim 1, wherein the oxygen prodrug comprises sodium percarbonate or carbamide peroxide, wherein the catalyst comprises catalase, and wherein, upon reaching the target site in the intestine of the subject, the oral formulation provides an increase of 2-5% oxygen at the target site for 24 hours or more, as compared to pretreatment oxygen concentration.

4. The oral formulation of claim 1, wherein the oral formulation provides an increase of 5-10% oxygen at the target site for 6 hours or more, as compared to pretreatment oxygen concentration.

5. The oral formulation of claim 1, wherein the oxygen prodrug is provided in a range of 250 to 2000 mg.

6. The oral formulation of claim 1, wherein the catalyst is provided in a range of 10 to 150 Baker units.

7. The oral formulation of claim 1, further comprising one or more binding agents, one or more dispersants, or one or more glidant and/or plasticizer.

8. The oral formulation of claim 1, wherein the formulation does not comprise a tannin or tannin-like component.

9. An oral formulation in solid form for inhibiting intestinal anaerobic bacteria, comprising:
    a plurality of granules or particles contained within a capsule, wherein each granule or particle comprises an oxygen prodrug and a catalyst,
        wherein the catalyst controls the rate of conversion of the oxygen prodrug to oxygen at a target site in an intestine of a subject;
    a first coating on an exterior of each granule, wherein the first coating is resistant to degradation in low pH environments;
    a second porous coating between the first coating and the catalyst, wherein the second porous coating has a pore size that controls diffusion of the catalyst across the second porous coating and allows for water to contact and activate the catalyst upon at least partial degradation of the first coating,
    a third controlled release coating between the oxygen prodrug and the catalyst, wherein the third controlled release coating is a barrier between the oxygen prodrug and the catalyst;
    wherein when orally administered to a subject and upon reaching the target site in the intestine of the subject, the catalyst catalyzes conversion of the oxygen prodrug to generate oxygen and create an aerobic environment at the target site in the intestine of the subject sufficient to inhibit growth or toxicity of a population of anaerobic bacteria in the intestine.

10. The oral formulation of claim 9, wherein the first coating is resistant to degradation in the stomach of the subject, thereby allowing the granules to be delivered to the target site of the intestine without being substantially inactivated by gastric acid.

11. The oral formulation of claim 9, further comprising one or more binding agents, one or more dispersants, or one or more glidant and/or plasticizer.

12. The oral formulation of claim 9, wherein the formulation does not comprise a tannin or tannin-like component.

13. The oral formulation of claim 9,
    wherein the population of anaerobic bacteria comprises *Clostridioides difficile*,
    wherein the oxygen prodrug is selected from sodium percarbonate, hydrogen peroxides, endoperoxides, carbamide peroxide, calcium peroxide, magnesium peroxide, and combinations thereof, and
    wherein the catalyst is selected from catalase, iodide, manganese dioxide, iron (III), silver, dichromate, and combinations thereof.

14. The oral formulation of claim 9, wherein the oxygen prodrug comprises sodium percarbonate or carbamide peroxide, wherein the catalyst comprises catalase, and wherein, upon reaching the target site in the intestine of the subject, the oral formulation provides an increase of 2-5% oxygen at the target site for 24 hours or more, as compared to pretreatment oxygen concentration.

15. The oral formulation of claim 9, wherein the oral formulation provides an increase of 5-10% oxygen at the target site for 6 hours or more, as compared to pretreatment oxygen concentration.

16. The oral formulation of claim 9, wherein the oxygen prodrug is provided in a range of 250 to 2000 mg and wherein the catalyst is provided in a range of 10 to 150 Baker units.

* * * * *